United States Patent
Schottek et al.

(10) Patent No.: US 7,049,453 B2
(45) Date of Patent: May 23, 2006

(54) "CONSTRAINED GEOMETRY" METALLOCENES, METHOD FOR THE PRODUCTION THEREOF AND USE OF THE SAME FOR THE POLYMERISATION OF OLEFINS

(75) Inventors: Jörg Schottek, Frankfurt (DE); Tim Dickner, Frankfurt (DE); Jörg Ludwig Schulte, Frankfurt (DE)

(73) Assignee: Celanese Ventures GmbH (DE)

( * ) Notice: Subject to any disclaimer, the term of this patent is extended or adjusted under 35 U.S.C. 154(b) by 0 days.

(21) Appl. No.: 10/508,238

(22) PCT Filed: Mar. 24, 2003

(86) PCT No.: PCT/EP03/03024

§ 371 (c)(1),
(2), (4) Date: Apr. 7, 2005

(87) PCT Pub. No.: WO03/080684

PCT Pub. Date: Oct. 2, 2003

(65) Prior Publication Data

US 2005/0187396 A1  Aug. 25, 2005

(30) Foreign Application Priority Data

Mar. 23, 2002  (DE) ................................ 102 13 191

(51) Int. Cl.
*C07F 17/00* (2006.01)
*B01J 31/00* (2006.01)
*C08F 4/44* (2006.01)

(52) U.S. Cl. ........................... 556/11; 556/12; 556/28; 556/43; 556/45; 556/53; 556/58; 556/136; 556/140; 526/127; 526/160; 526/943; 502/103; 502/117; 502/119

(58) Field of Classification Search ................... 556/11, 556/12, 28, 43, 45, 53, 58, 136, 140; 526/127, 526/160, 943; 502/103, 117, 119
See application file for complete search history.

(56) References Cited

FOREIGN PATENT DOCUMENTS

| DE | 19622207 A1 | 12/1997 |
|---|---|---|
| EP | 0302424 A1 | 2/1989 |
| EP | 0601830 A2 | 6/1994 |
| EP | 0811627 A2 | 12/1997 |
| EP | 0824112 A1 | 2/1998 |
| EP | 0824113 A1 | 2/1998 |
| EP | 0924223 A2 | 6/1999 |
| WO | WO 94/28034 A1 | 12/1994 |
| WO | WO 97/11775 A2 | 4/1997 |
| WO | WO 98/27103 A1 | 6/1998 |
| WO | WO 99/40129 A1 | 8/1999 |

*Primary Examiner*—Porfirio Nazario-Gonzalez
(74) *Attorney, Agent, or Firm*—Hammer & Hanf, P.C.

(57) ABSTRACT

The present invention relates to a process for preparing specific transition metal compounds, novel transition metal compounds and also catalyst systems and their use for the homo- or copolymerization of olefins.

20 Claims, No Drawings

"CONSTRAINED GEOMETRY" METALLOCENES, METHOD FOR THE PRODUCTION THEREOF AND USE OF THE SAME FOR THE POLYMERISATION OF OLEFINS

The present invention relates to a process for preparing specific transition metal compounds, novel transition metal compounds and their use for the polymerization of olefins.

In recent years, olefin polymerization has been carried out using not only conventional Ziegler catalysts but also metallocenes to generate polyolefins having particular properties which are not achieved using conventional Ziegler catalysts. Metallocenes can, if appropriate in combination with one or more cocatalysts, be used as catalyst components for the polymerization and copolymerization of olefins. In particular, halogen-containing metallocenes are used as catalyst precursors which can be converted, for example by means of an aluminoxane, into a polymerization-active cationic metallocene complex.

However, the preparation and use of metallocenes is still a cost factor which has not been able to be overcome either by means of increased activity or by means of improved synthetic methods. In addition, making such catalysts heterogeneous presents a further problem, since this greatly decreases the activities compared to the polymerization carried out by homogeneous catalysis.

Various "constrained-geometry" catalysts are described in the literature, e.g. in EP 416 815. These catalysts are bridged cyclopentadienylamido-metal complexes which are able to polymerize various olefins. Furthermore, WO 98/27103 describes indenyl systems of the "constrained-geometry" type which are able to catalyse olefin polymerization. However, "constrained-geometry" catalysts are not able to polymerize propene isospecifically and the polymers obtained using these catalysts are atactic (Waymouth, R. M. et al., Polym. Prepr. 1996, 37(2), 474). It is therefore an object of the invention to develop new transition metal catalysts for the isospecific polymerization of olefins which avoid the disadvantages of the prior art described.

It has surprisingly been found that bridged complexes containing a pentacoordinating cyclic system and a heterocycle having at least two donor atoms are able to polymerize propene isospecifically.

The present invention accordingly provides compounds of the formulae Ia and Ib,

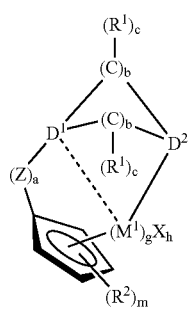

Formula Ia

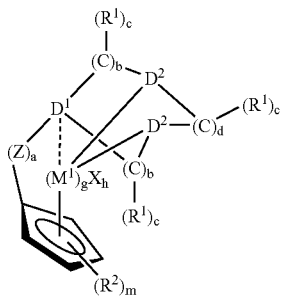

Formula Ib where $M^1$ is a metal of groups III to X of the Periodic Table of the Elements, in particular Sc, Y, La, Ti, Zr, Hf, V, Nb, Ta, Cr, Mo, W, Mn, Tc, Re, Fe, Ru, Os, Co, Rh, Ir, Ni, Pd or Pt and the radicals $D^1$ are identical or different and are each a donor atom of group XV of the Periodic Table of the Elements, and the radicals $D^2$ are identical or different and are each a donor atom of group XV of the Periodic Table of the Elements, and Z is a bridging structural element between the donor atom $D^1$ and the pentacoordinating cyclic system and the radicals X are identical or different and are each a hydrogen atom, a $C_1$–$C_{20}$-hydrocarbon group or a halogen atom or $OR^3$, $SR^3$, $OSO_2R^3$, $OSi(R^3)_3$, $Si(R^3)_3$, $P(R^3)_2$, $P(R^3)_3$, $NCR^3$, $N(R^3)_3$, $B(R^3)_4$, substituted or unsubstituted pyridine or $N(R^3)_2$, and the radicals $R^1$ are identical or different and are each a hydrogen atom, a $C_1$–$C_{20}$-alkyl group, a $C_6$–$C_{20}$-aryl group, a $C_7$–$C_{20}$-alkylaryl group, a $C_7$–$C_{30}$-arylalkyl group, a $C_2$–$C_{20}$-alkenyl group, a $C_2$–$C_{20}$-alkynyl group or a halogen-containing $C_1$–$C_{20}$-alkyl group, $C_6$–$C_{20}$-aryl group, $C_7$–$C_{20}$-alkylaryl group, $C_7$–$C_{30}$-arylalkyl group, $C_2$–$C_{20}$-alkenyl group, $C_2$–$C_{20}$-alkynyl group or a heteroatom-containing $C_1$–$C_{20}$-alkyl group, $C_6$–$C_{20}$-aryl group, $C_7$–$C_{20}$-alkylaryl group, $C_7$–$C_{30}$-arylalkyl group, $C_2$–$C_{20}$-alkenyl group, $C_2$–$C_{20}$-alkynyl group or $Si(R^3)_3$, where one or more radicals $R^1$ together with one or more radicals $R^1$ may form a monocyclic or polycyclic ring system, and the radicals $R^2$ are identical or different and are each a hydrogen atom, $Si(R^3)_3$, a $C_1$–$C_{30}$ group which together with the cyclopentadienyl ring may form an azapentalene, thiapentalene or phosphapentalene, or two or more radicals $R^2$ may be joined to one another so that the radicals $R^2$ and the atoms of the cyclopentadienyl ring which connect them form a $C_4$–$C_{24}$ ring system which may in turn be substituted by $R^3$, the radicals $R^3$ are identical or different and are each a hydrogen atom, a halogen atom, a $C_1$–$C_{10}$-alkyl group, a $C_6$–$C_{20}$-aryl group, a $C_7$–$C_{20}$-alkylaryl group, a $C_7$–$C_{30}$-arylalkyl group, a $C_2$–$C_{20}$-alkenyl group, a $C_2$–$C_{20}$-alkynyl group or a halogen-containing $C_1$–$C_{20}$-alkyl group, $C_6$–$C_{20}$-aryl group, $C_7$–$C_{20}$-alkylaryl group, $C_7$–$C_{30}$-arylalkyl group, $C_2$–$C_{20}$-alkenyl group, $C_2$–$C_{20}$-alkynyl group or a heteroatom-containing $C_1$–$C_{20}$-alkyl group, $C_6$–$C_{20}$-aryl group, $C_7$–$C_{20}$-alkylaryl group, $C_7$–$C_{30}$-arylalkyl group, $C_2$–$C_{20}$-alkenyl group, $C_2$–$C_{20}$-alkynyl group, and a is an integer from 0 to 10, and when a=0, $D^1$ forms a covalent bond to the pentacoordinating cyclic system, and the indices b are identical or different and are each an integer from 1 to 10, and the indices c are identical or different and are each an integer from 1 to 10, and d is an integer from 1 to 10, and g is an integer from 1 to 3, and h is an integer from 1 to 4, and m is 4.

Illustrative but nonlimiting examples of bridging structural elements Z are: $CH_2$, $C(CH_3)H$, $C(CH_3)_2$, $C(C_2H_5)H$, $C(C_2H_5)(CH_3)$, $C(C_2H_5)_2$, $C(Ph)H$, $C(Ph)(CH_3)$, $C(Ph)(C_2H_5)$, $C(Ph)_2$, $CH_2CH_2$, $C(CH_3)HCH_2$, $C(CH_3)_2CH_2$, $C(CH_3)_2C(CH_3)H$, $C(CH_3)_2C(CH_3)_2$, $C(Ph)HC(Ph)H$, $C(CH_2)_2$, $C(CH_2)_3$, $C(CH_2)_4$, $C(CH_2)_5$, $C(CH_2)_6$, $o-C_6H_4$, $m-C_6H_4$, $p-C_6H_4$, $o-C_{10}H_6$, $m-C_{10}H_6$, $p-C_{10}H_6$, 2,2'-(1,1'-biphenyl), 2,2'-(1,1'-binaphthyl), $Si(CH_3)_2$, $Si(CH_3)(Si(CH_3)_3)$, $Si(Si(CH_3)_3)_2$, $Si(Ph)Me$, $Si(Ph)_2$, $Si(CH_3)_2Si(CH_3)_2$, $Si(CH_2)_2$, $Si(CH_2)_3$, $Si(CH_2)_4$, $Si(CH_2)_5$, $Si(CH_2)_6$ and $Ge(Ch_3)_2$.

For the purposes of the present invention, a $C_1$–$C_{40}$ group is preferably $C_1$–$C_{40}$-alkyl, in particular $C_1$–$C_{20}$-alkyl, particularly preferably methyl, ethyl, n- or i-propyl, tert-butyl, n-pentyl, n-hexyl, cyclohexyl or octyl, $C_1$–$C_{10}$-fluoroalkyl, $C_1$–$C_{12}$-alkoxy, $C_6$–$C_{20}$-aryl, in particular phenyl, biphenyl, phenyl, tolyl, xylenyl, mesityl, p-methoxyphenyl, p-t-butylphenyl or naphthyl, $C_5$–$C_{20}$-heteroaryl, in particular pyridyl, pyridazinyl, pyrimidinyl, pyrazinyl, quinolinyl or borataphenyl, furyl, benzofuryl or thiophenyl, $C_6$–$C_{10}$-fluoroaryl, in particular tetrafluorophenyl, $C_6$–$C_{10}$-aryloxy, $C_2$–$C_{10}$-alkenyl, $C_7$–$C_{40}$-arylalkyl, $C_7$–$C_{40}$-alkylaryl, $C_5$–$C_{24}$-heteroaryl or $C_8$–$C_{40}$-arylalkenyl For the purposes of the present invention, the term $C_1$–$C_{30}$ group preferably refers to $C_1$–$C_{30}$-alkyl, in particular methyl, ethyl, n- or i-propyl, tert-butyl, n-pentyl, n-hexyl, cyclohexyl or octyl, $C_2$–$C_{25}$-alkenyl, $C_3$–$C_{15}$-alkylalkenyl, $C_6$–$C_{24}$-aryl, in particular phenyl and biphenyl, $C_5$–$C_{24}$-heteroaryl, $C_7$–$C_{30}$-arylalkyl, $C_7$–$C_{30}$-alkylaryl, fluorinated $C_1$–$C_{25}$-alkyl, fluorinated $C_6$–$C_{24}$-aryl, in particular tetrafluorophenyl, fluorinated $C_7$–$C_{30}$-arylalkyl, fluorinated $C_7$–$C_{30}$-alkylaryl or $C_1$–$C_{10}$-alkoxy.

For the purposes of the present invention, a $C_1$–$C_{20}$ group is preferably $C_1$–$C_{20}$-alkyl, in particular $C_1$–$C_{10}$-alkyl, preferably methyl, ethyl, n- or i-propyl, tert-butyl, n-pentyl, n-hexyl, cyclohexyl or octyl, $C_1$–$C_{10}$-fluoroalkyl, $C_1$–$C_{12}$-alkoxy, $C_6$–$C_{20}$-aryl, in particular $C_6$–$C_{10}$-aryl, particularly preferably phenyl, biphenyl, phenyl, tolyl, xylenyl, mesityl, p-methoxyphenyl, p-butylphenyl or naphthyl, $C_5$–$C_{20}$-heteroaryl, in particular pyridyl, pyridazinyl, pyrimidinyl, pyrazinyl, quinolinyl or borataphenyl, furyl, benzofuryl or thiophenyl, $C_6$–$C_{10}$-fluoroaryl, in particular tetrafluorophenyl, $C_6$–$C_{10}$-aryloxy, $C_2$–$C_{20}$-alkenyl, $C_2$–$C_{20}$-alkynyl, $C_7$–$C_{20}$-arylalkyl, $C_7$–$C_{20}$-alkylaryl, $C_5$–$C_{24}$-heteroaryl or $C_8$–$C_{20}$-arylalkenyl.

Preference is given to transition metal compounds of the formulae Ia and Ib in which $M^1$ is a metal of groups III to X of the Periodic Table of the Elements, in particular Sc, Y, La, Ti, Zr, Hf, V, Nb, Ta, Cr, Mo, W, Mn, Re, Fe, Ru, Co, Rh, Ir, Ni, Pd or Pt and the radicals $D^1$ are identical or different and are each a donor atom of group XV of the Periodic Table of the Elements, in particular N or P, and the radicals $D^2$ are identical or different and are each a donor atom of the group XV of the Periodic Table of the Elements, in particular N or P, and Z is a bridging structural element between the donor atom $D^1$ and the pentacoordinating cyclic system and the radicals X are identical or different and are each a hydrogen atom, a $C_1$–$C_{10}$-hydrocarbon group such as $C_1$–$C_{10}$-alkyl, $C_6$–$C_{10}$-aryl, $C_7$–$C_{10}$-alkylaryl $C_7$–$C_{10}$-arylalkyl, $C_2$–$C_{10}$-alkenyl, $C_2$–$C_{10}$-alkynyl or a halogen atom or $OR^3$, $SR^3$, $OSO_2R^3$, $OSi(R^3)_3$, $Si(R^3)_3$, $P(R^3)_2$, $P(R^3)_3$, $NCR^3$, $N(R^3)_3$, $B(R^3)_4$, substituted or unsubstituted pyridine or $N(R^3)_2$, and the radicals $R^1$ are identical or different and are each a hydrogen atom, a $C_1$–$C_{10}$-alkyl group, a $C_6$–$C_{10}$-aryl group, a $C_7$–$C_{10}$-alkylaryl group, a $C_7$–$C_{10}$-arylalkyl group, a $C_2$–$C_{10}$-alkenyl group, a $C_2$–$C_{10}$-alkynyl group or a halogen-containing $C_1$–$C_{10}$-alkyl group, $C_6$–$C_{10}$-aryl group, $C_7$–$C_{10}$-alkylaryl group, $C_7$–$C_{10}$-arylalkyl group, $C_2$–$C_{10}$-alkenyl group, $C_2$–$C_{10}$-alkynyl group or a heteroatom-containing $C_1$–$C_{10}$-alkyl group, $C_6$–$C_{10}$-aryl group, $C_7$–$C_{10}$-alkylaryl group, $C_7$–$C_{10}$-arylalkyl group, $C_2$–$C_{10}$-alkenyl group, $C_2$–$C_{10}$-alkynyl group or $Si(R^3)_3$, where one or more radicals $R^1$ together with one or more radicals $R^1$ may form a monocyclic or polycyclic ring system, and the radicals $R^2$ are identical or different and are each a hydrogen atom, $Si(R^3)_3$, a $C_1$–$C_{30}$ group such as $C_1$–$C_{25}$-alkyl such as methyl, ethyl, tert-butyl, cyclohexyl or octyl, $C_2$–$C_{25}$-alkenyl, $C_3$–$C_{15}$-alkylalkenyl, $C_6$–$C_{24}$-aryl, $C_5$–$C_{24}$-heteroaryl which together with the cyclopentadienyl ring form an azapentalene, thiapentalene or phosphapentalene, $C_7$–$C_{30}$-arylalkyl, $C_7$–$C_{30}$-alkylaryl, fluorinated $C_1$–$C_{25}$-alkyl, fluorinated $C_6$–$C_{24}$-aryl, fluorinated $C_7$–$C_{30}$-arylalkyl, fluorinated $C_7$–$C_{30}$-alkylaryl or $C_1$–$C_{12}$-alkoxy, or two or more radicals $R^2$ may be joined to one another so that the radicals $R^2$ and the atoms of the cyclopentadienyl ring which connect them may form a $C_4$–$C_{24}$ ring system which may in turn be substituted by $R^4$, the radicals $R^3$ are identical or different and are each a hydrogen atom, a halogen atom, a $C_1$–$C_{10}$-alkyl group, a $C_6$–$C_{10}$-aryl group, a $C_7$–$C_{10}$-alkylaryl group, a $C_7$–$C_{10}$-arylalkyl group, a $C_2$–$C_{10}$-alkenyl group, a $C_2$–$C_{10}$-alkynyl group or a halogen-containing $C_1$–$C_{10}$-alkyl group, $C_6$–$C_{10}$-aryl group, $C_7$–$C_{10}$-alkylaryl group, $C_7$–$C_{20}$-arylalkyl group, $C_2$–$C_{10}$-alkenyl group, $C_2$–$C_{10}$-alkynyl group or a heteroatom-containing $C_1$–$C_{10}$-alkyl group, $C_6$–$C_{10}$-aryl group, $C_7$–$C_{10}$-alkylaryl group, $C_7$–$C_{20}$-arylalkyl group, $C_2$–$C_{10}$-alkenyl group, $C_2$–$C_{10}$-alkynyl group, and a is an integer from 0 to 5, and when a=0, $D^1$ forms a covalent bond to the pentacoordinating cyclic system, and the indices b are identical or different and are each an integer from 1 to 7, and the indices c are identical or different and are each an integer from 1 to 10, and d is an integer from 1 to 7, and g is an integer from 1 to 2, and h is an integer from 1 to 4, and m is 4.

Very particular preference is given to transition metal compounds of the formulae Ia and Ib in which $M^1$ is Ti, Zr, Hf, V, Nb, Cr, Mo, Mn, Fe, Ru, Co, Rh or Ni, and the radicals $D^1$ are identical or different and are each N or P and the radicals $D^2$ are identical or different and are each N or P and Z is a bridging structural element between the donor atom $D^1$ and the pentacoordinating cyclic system and the radicals X are identical or different and are each a hydrogen atom, fluoride, chloride, bromide, iodide, methyl, ethyl, butyl, benzyl, tolyl, ethenyl, ethynyl, phenoxide, dimethylamide, diphenylphosphine, triphenylphosphine, tetrakis(pentafluorophenyl)borate or pyridyl, and the radicals $R^1$ are identical or different and are each a hydrogen atom, a silyll group such as trimethylsilyl, triethylsilyl, tri-i-propylsilyll or triphenylsilyl, an alkyl group such as methyl, ethyl, propyl, butyl, i-propyl, s-butyl or t-butyl, an aryl group such as phenyl, tolyl, xylenyl, mesityl, p-methoxyphenyl, p-t-butylphenyl or naphthyl, a heteroaryl group such as pyridyl, pyridazinyl, pyrimidinyl, pyrazinyl, quinolinyl or borataphenyl, a heterocyclic group such as furyl, benzofuryl or thiophenyl, an alkylaryl group such as benzyl, an alkenyl group such as ethenyl, an alkynyl group such as ethynyl, a halogenated alkyl group such as trifluoromethyl or pentafluoroethyl, where one or more radicals $R^1$ together with one or more radicals $R^1$ may form a monocyclic or polycyclic ring system which may be substituted by one or more radicals $R^3$, e.g. piperazine, 1,4-dihydropyrazine, 2,6-dimethyl-1,4-dihydropyrazine, 2,6-diphenyl-1,4-dihydropyrazine, 5,10-dihydrophenazine, 2,3-dihydrobenzimidazole, 2,2-dimethyl-2,3-dihydrobenzimidazole, 2,2-di-i-propyl-2,3-dihydrobenzimidazole, or 1,3,5-triazinane, and the radicals $R^2$ are identical or different and are each a hydrogen atom, a silyll group such as trimethylsilyll, triethylsilyll, tri-i-propylsilyll or triphenylsilyll, an alkyl group such as methyl, ethyl, propyl, butyl, i-propyl, s-butyl or t-butyl, an aryl group such as phenyl tolyl, xylenyl, mesityl, p-methoxyphenyl, p-t-butylphenyl or naphthyl, a heteroaryl group such as pyridyl, pyridazinyl, pyrimidinyl, pyrazinyl, quinolinyl or borataphenyl, a heterocyclic group such as furyl, benzofuryl or thiophenyl, an alkylaryl group such as benzyl, an alkenyl group such as ethenyl, an alkynyl group such as ethynyl, a halogenated alkyl group such as trifluoromethyl or pentafluoroethyl, a heteroaryl group which together with the cyclopentadienyl ring may form an azapentalene, thiapentalene or phosphapentalene, or two or more radicals $R^2$ may be joined to one another so that the radicals $R^2$ and the atoms of the cyclopentadienyl ring which connect them form a polycyclic ring system, e.g. indenyl, fluorenyl or cyclopentaphenanthrene which may in turn be substituted by $R^3$, and the radicals $R^3$ are identical or different and are each a hydrogen atom, a silyll group such as trimethylsilyll, triethylsilyll, tri-i-propylsilyll or triphenylsilyll, an alkyl group such as methyl, ethyl, propyl, butyl, i-propyl, s-butyl or t-butyl, an aryl group such as phenyl, tolyl, xylenyl, mesityl, p-methoxyphenyl, p-t-butylphenyl or naphthyl, a heteroaryl group such as pyridyl, pyridazinyl, pyrimidinyl, pyrazinyl, quinolinyl or borataphenyl, a heterocyclic group such as furyl, benzofuryl or thiophenyl, an alkylaryl group such as benzyl, an alkenyl group such as ethenyl, an alkynyl group such as ethynyl, a halogenated alkyl group such as trifluoromethyl or pentafluoroethyl, and a is an integer from 0 to 2, and when a=0, $D^1$ forms a covalent bond to the pentacoordinating cyclic system, and the indices b are identical or different and are each an integer from 1 to 7, and the indices c are identical or different and are each an integer from 1 to 10, and d is an integer from 1 to 4, and g is 1 and, h is an integer from 1 to 3, and m is 4.

Examples of compounds of the formula Ia and Ib, which examples are illustrative but which do not restrict the invention are,

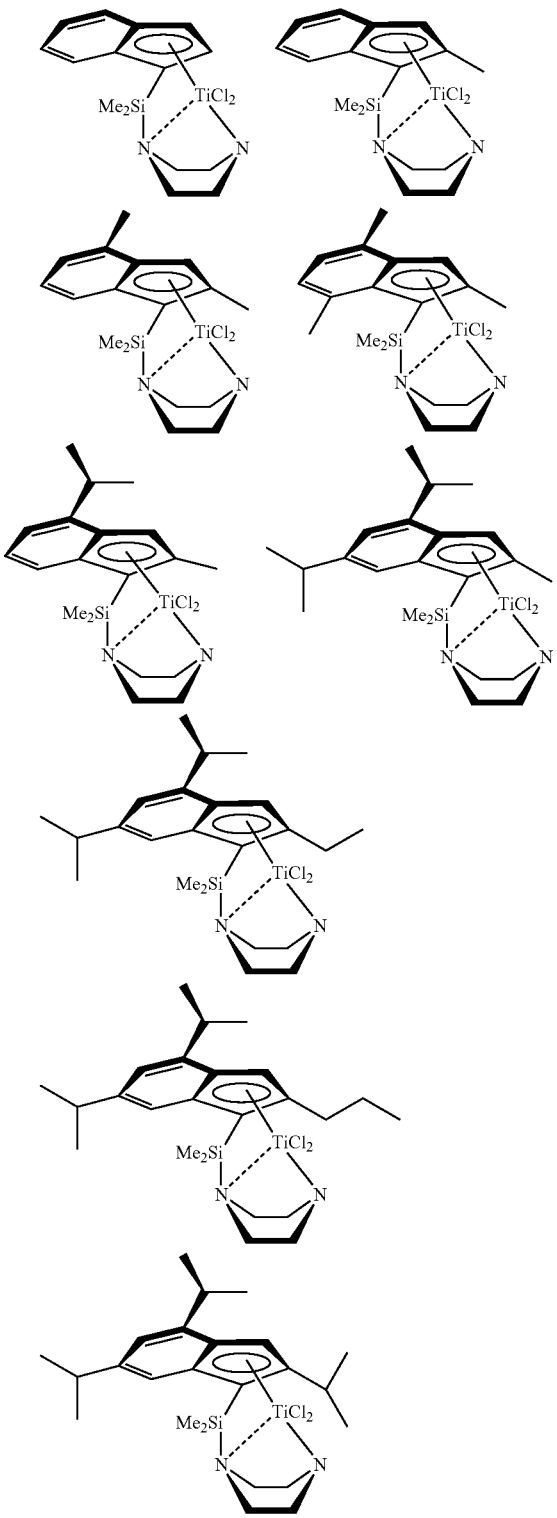

-continued
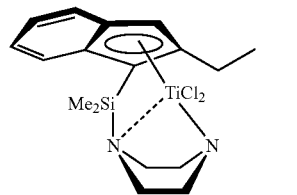
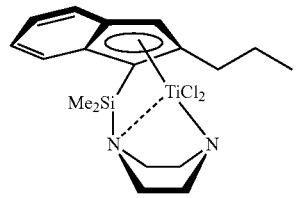
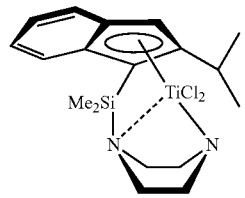
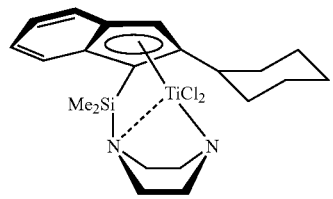
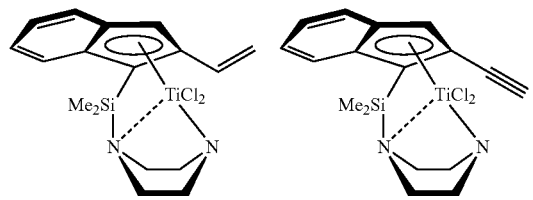
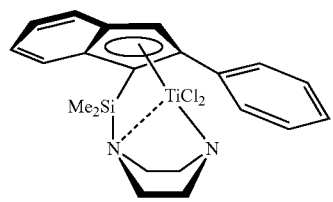
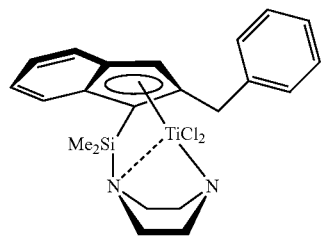
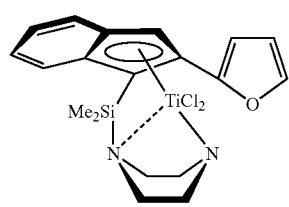
-continued
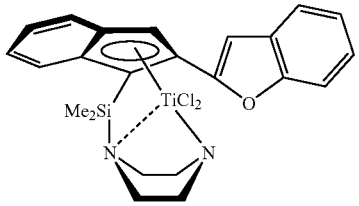
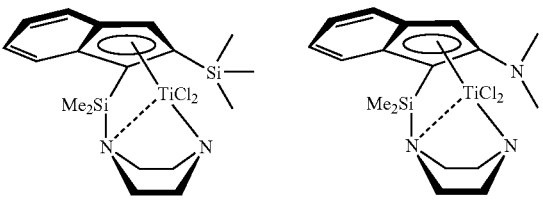
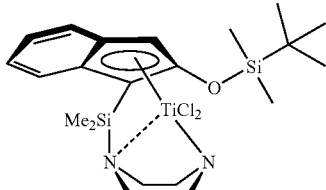
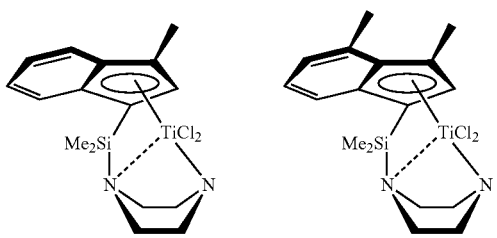
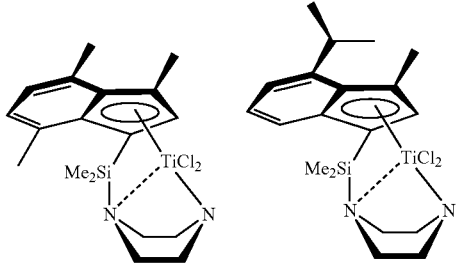
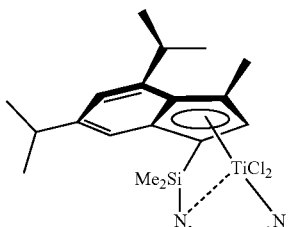
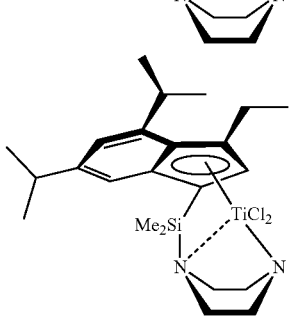

-continued
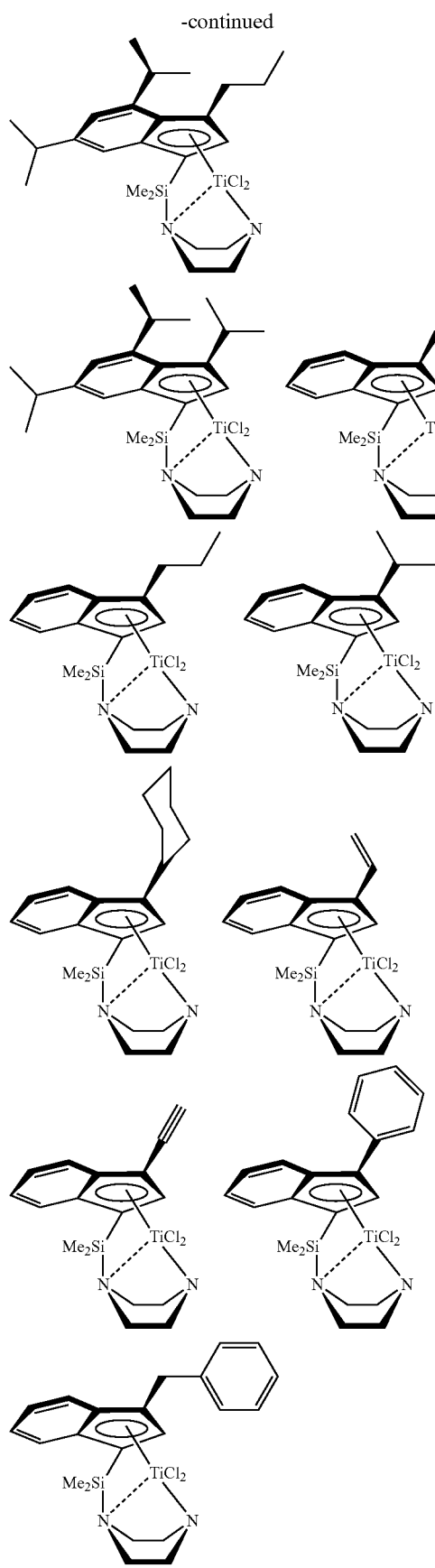
-continued
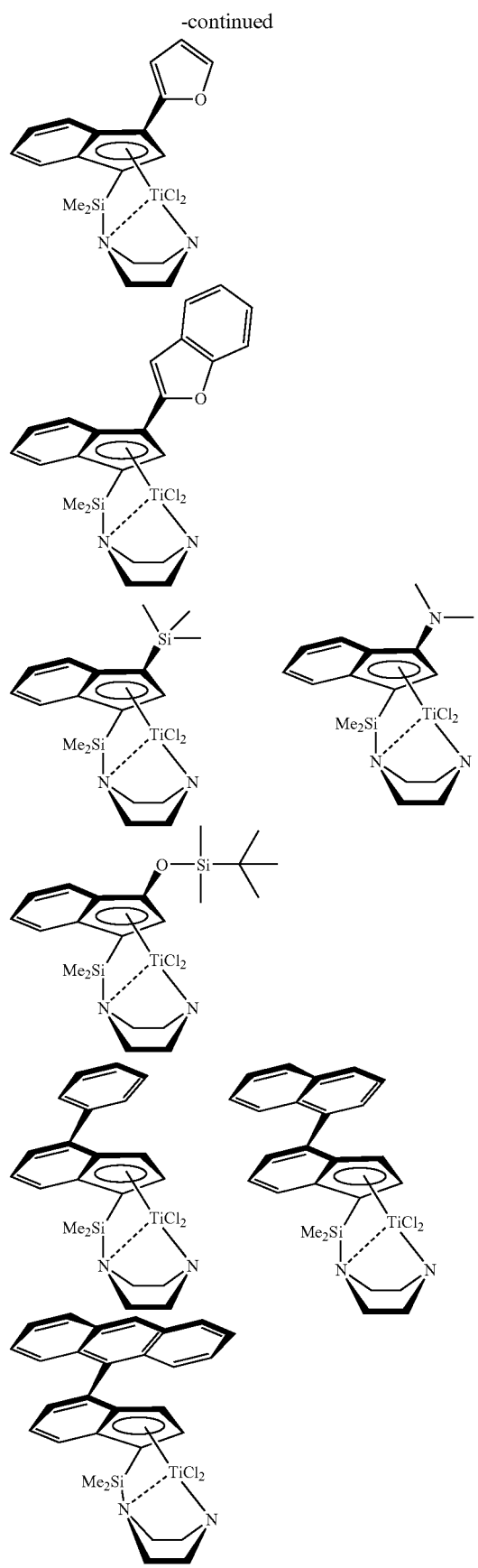

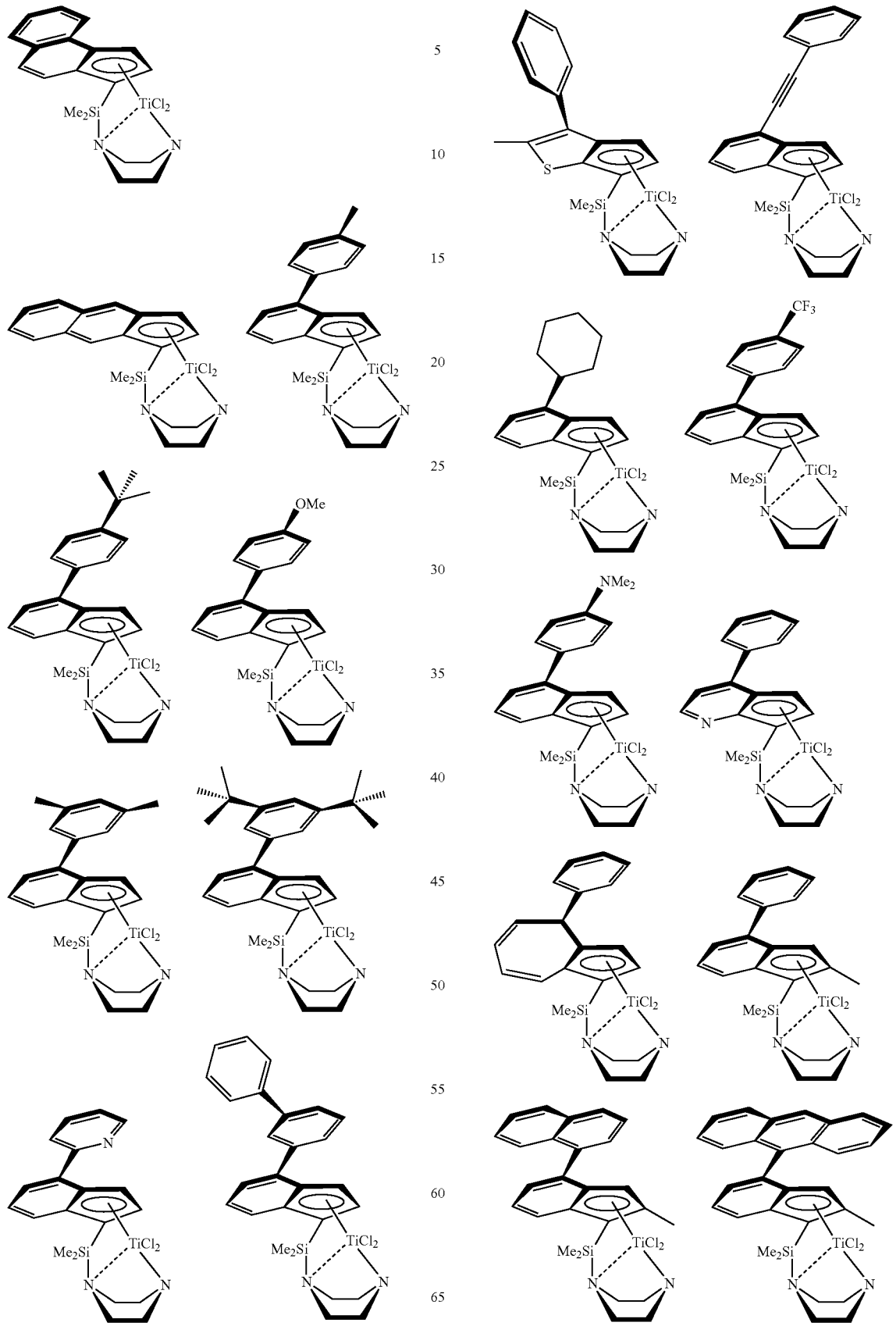

-continued
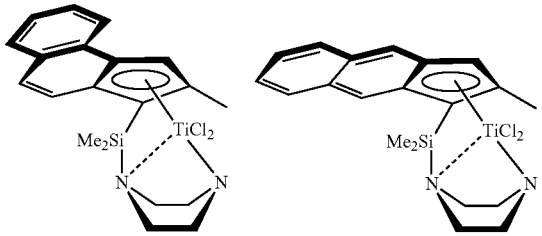
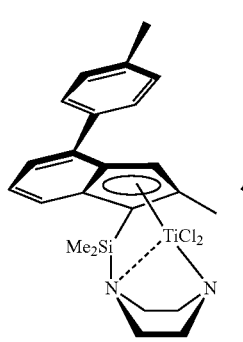
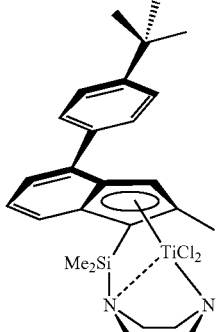
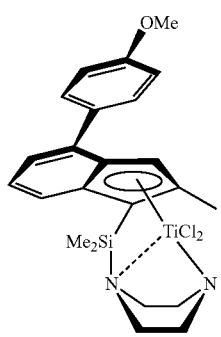
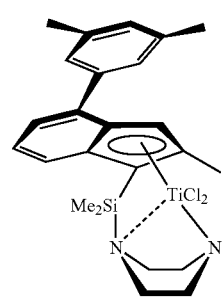
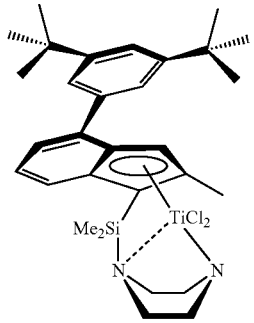
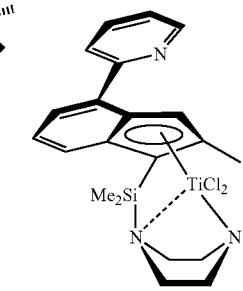
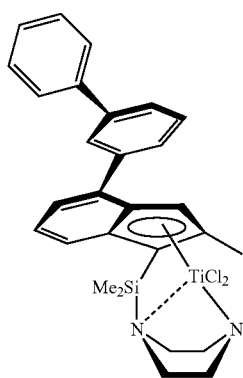
-continued
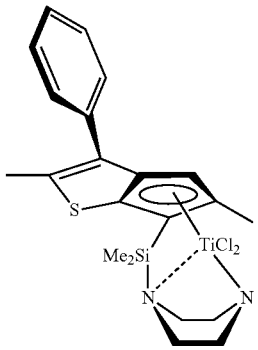
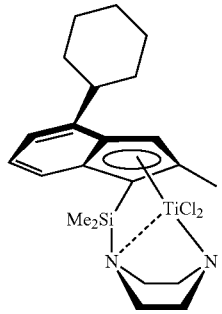
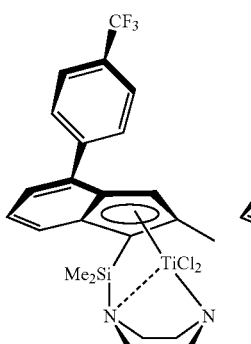
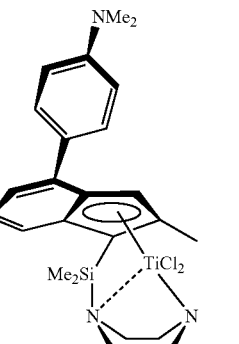
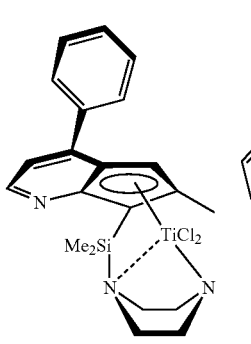
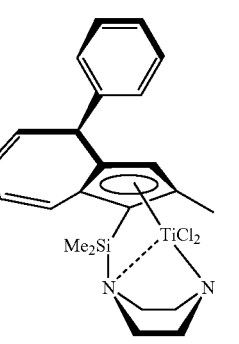
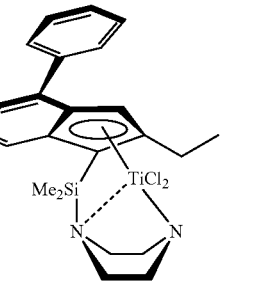
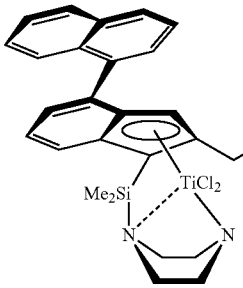
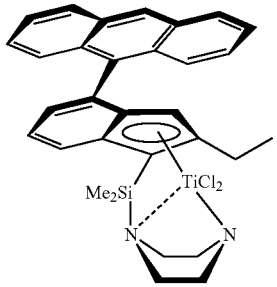

-continued
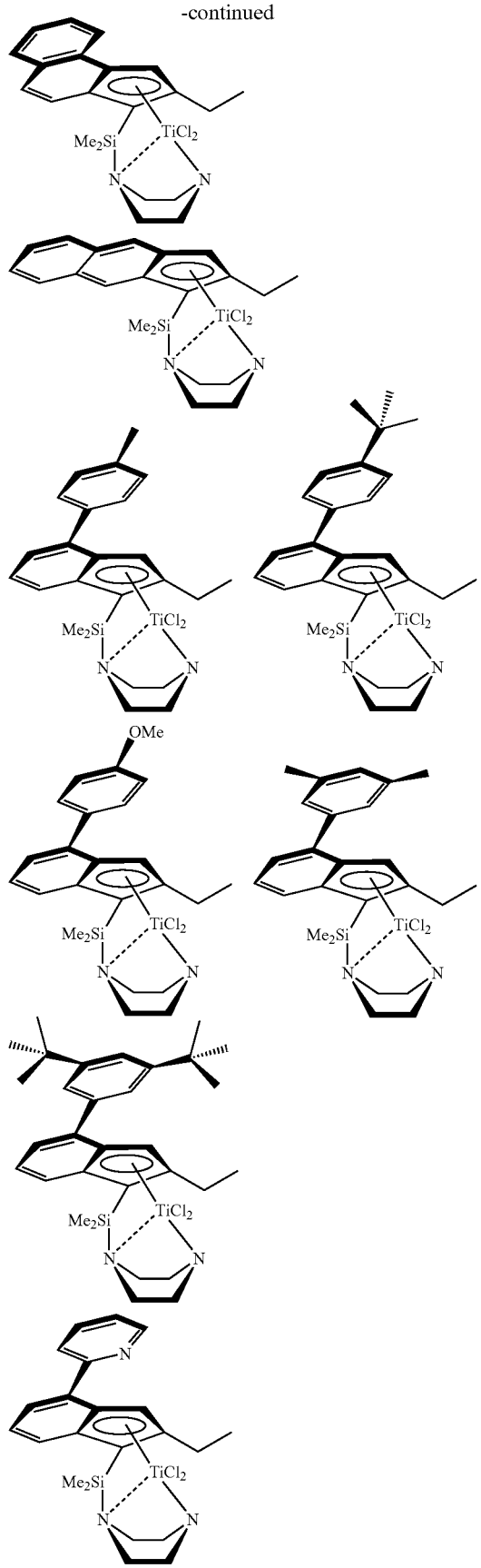
-continued
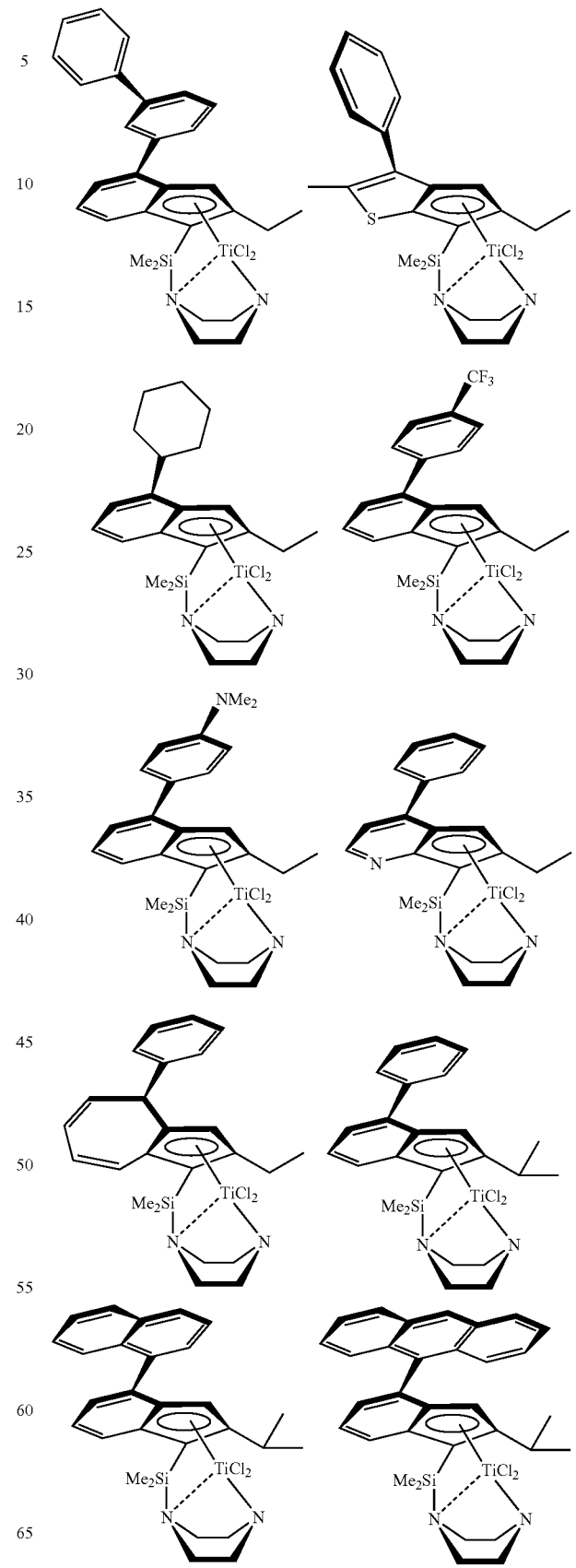

-continued
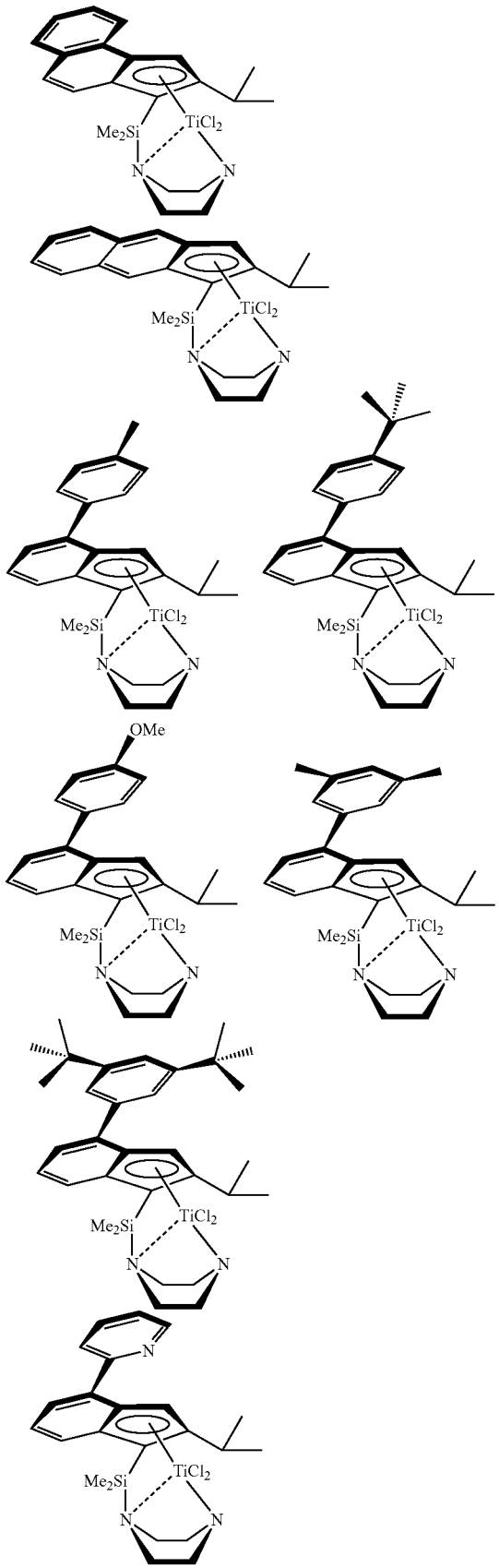
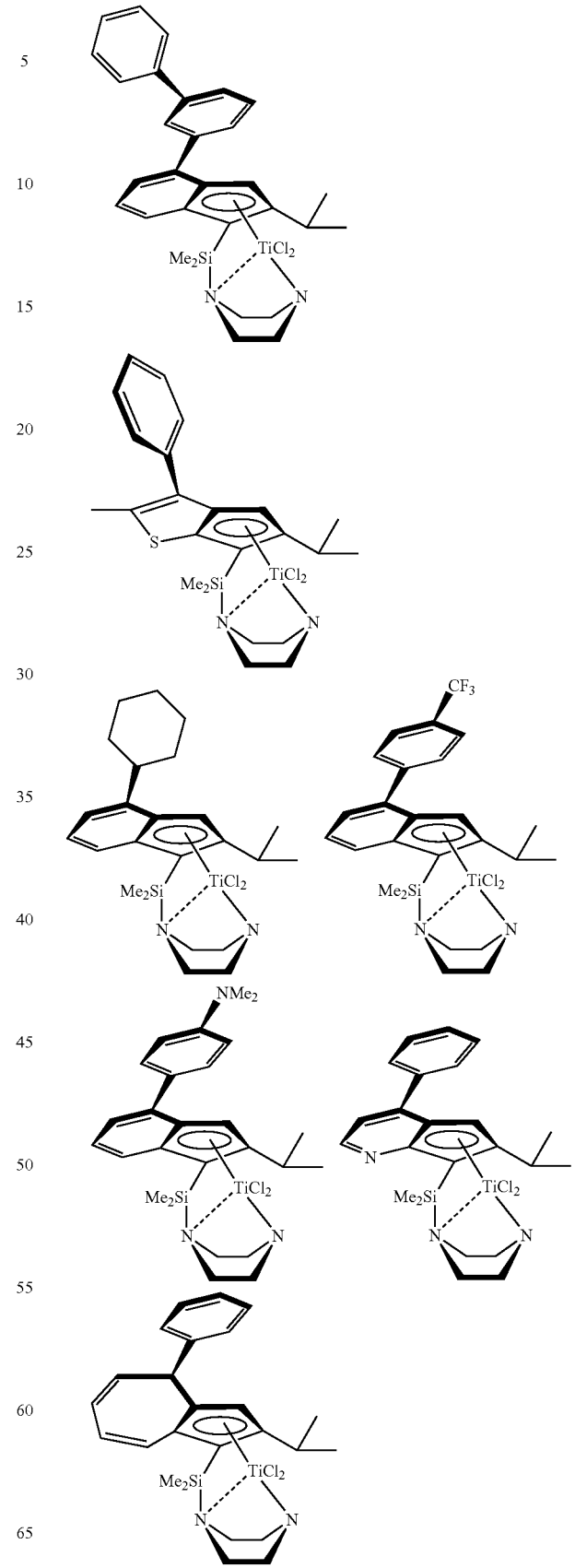

-continued
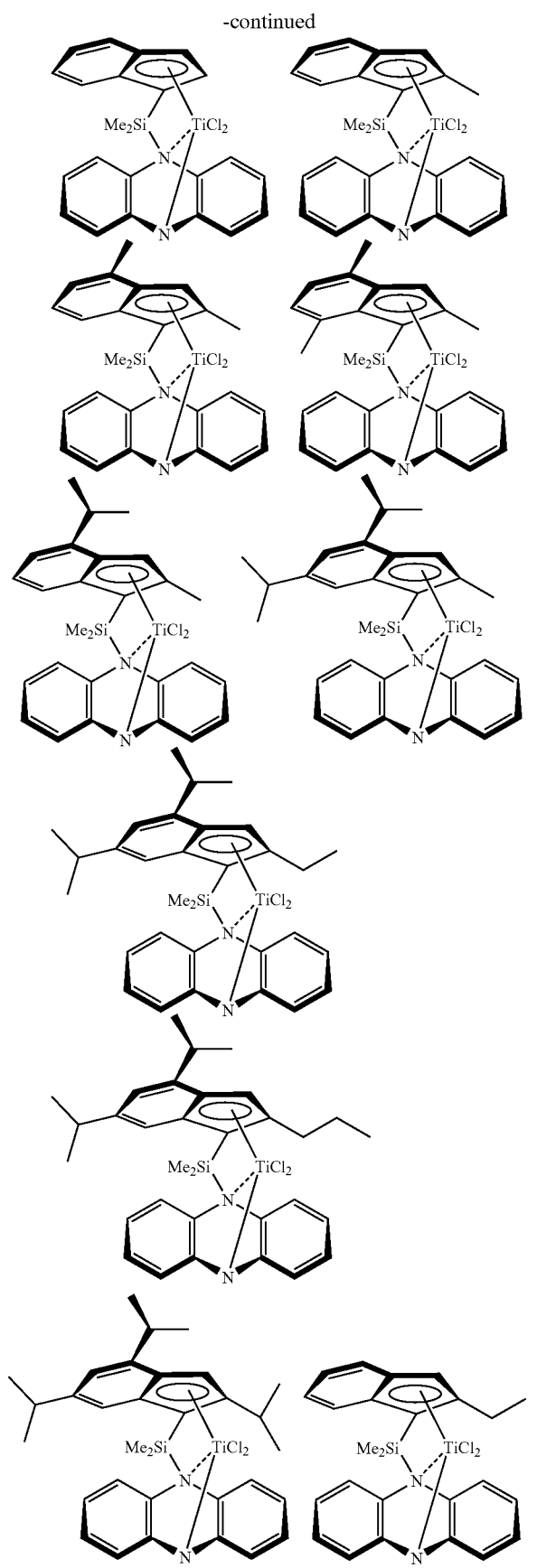
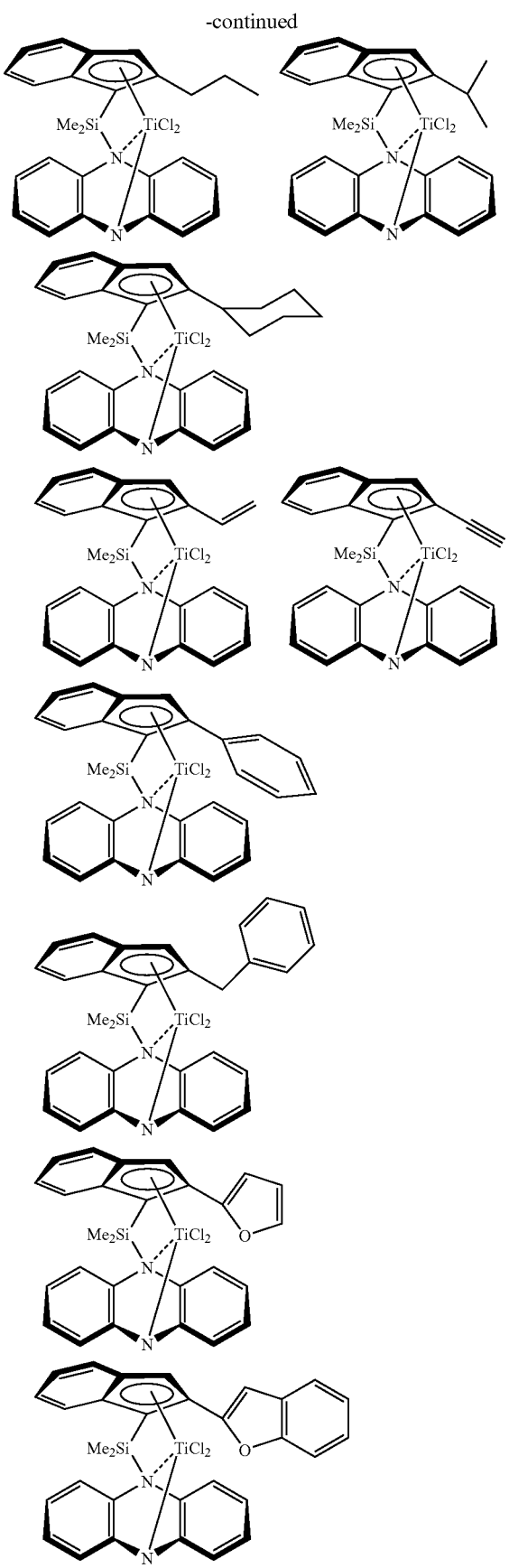

-continued
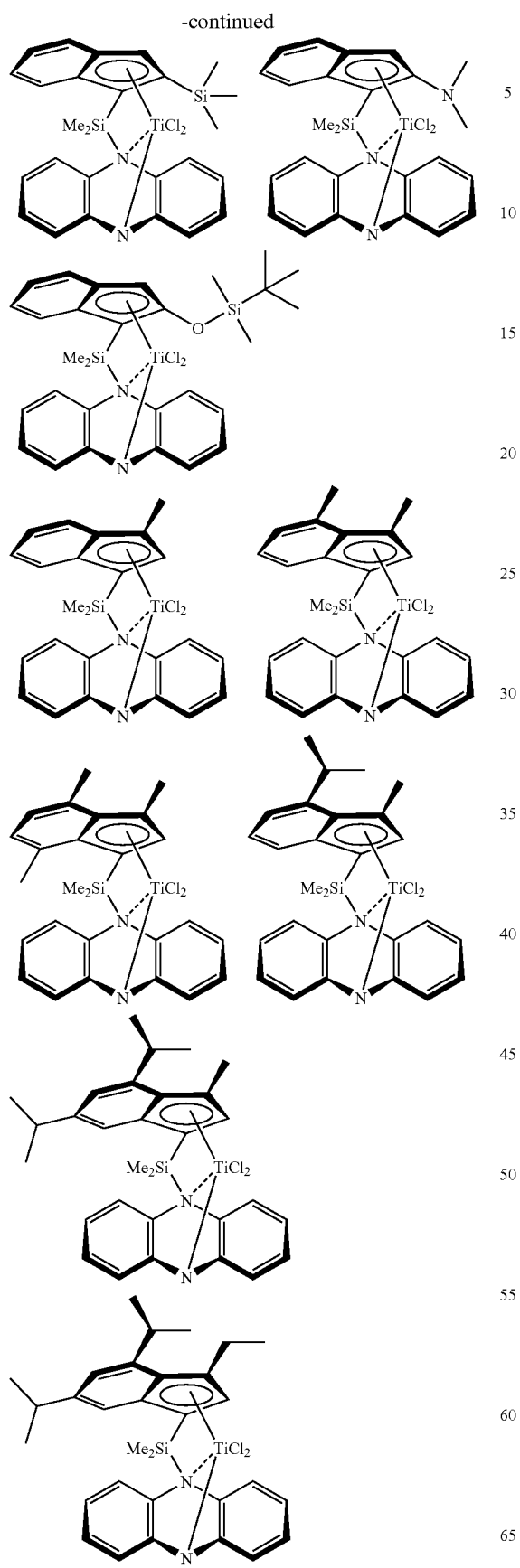
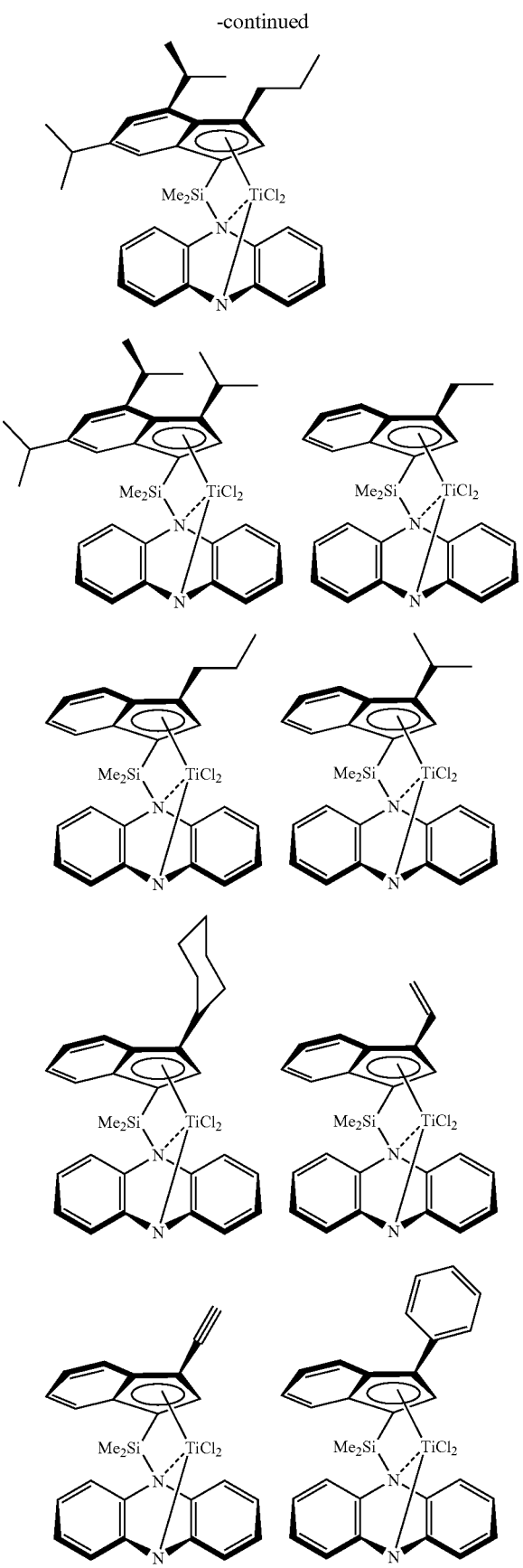

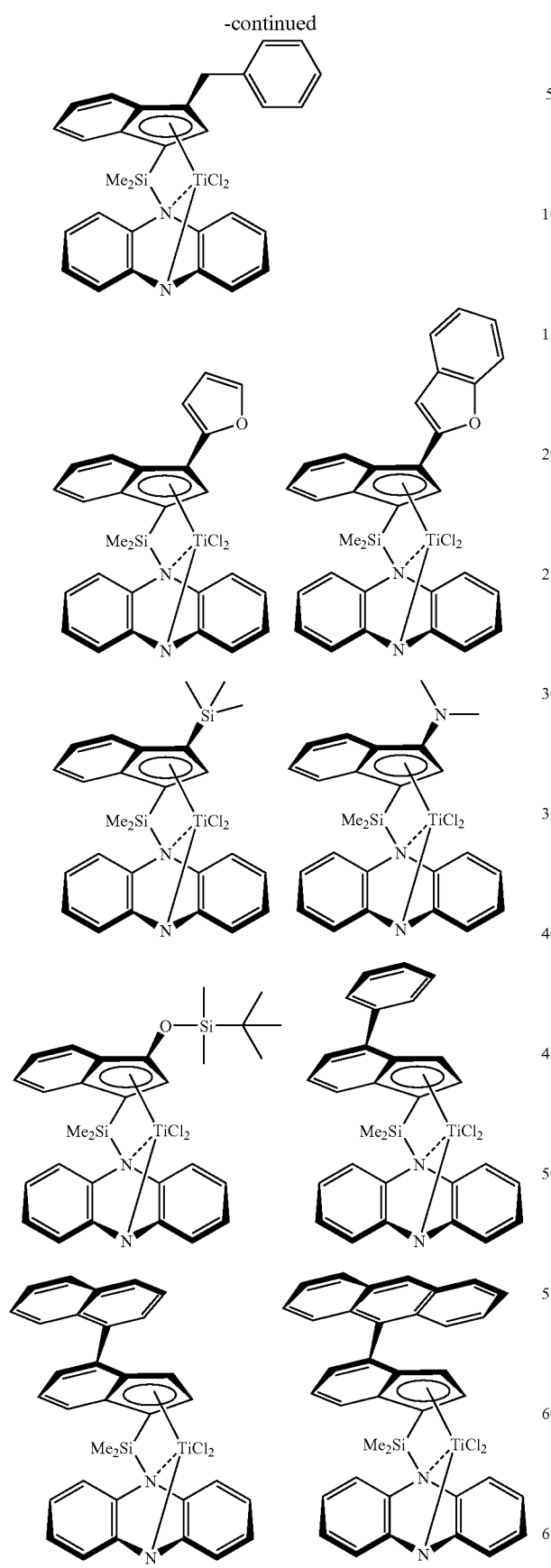
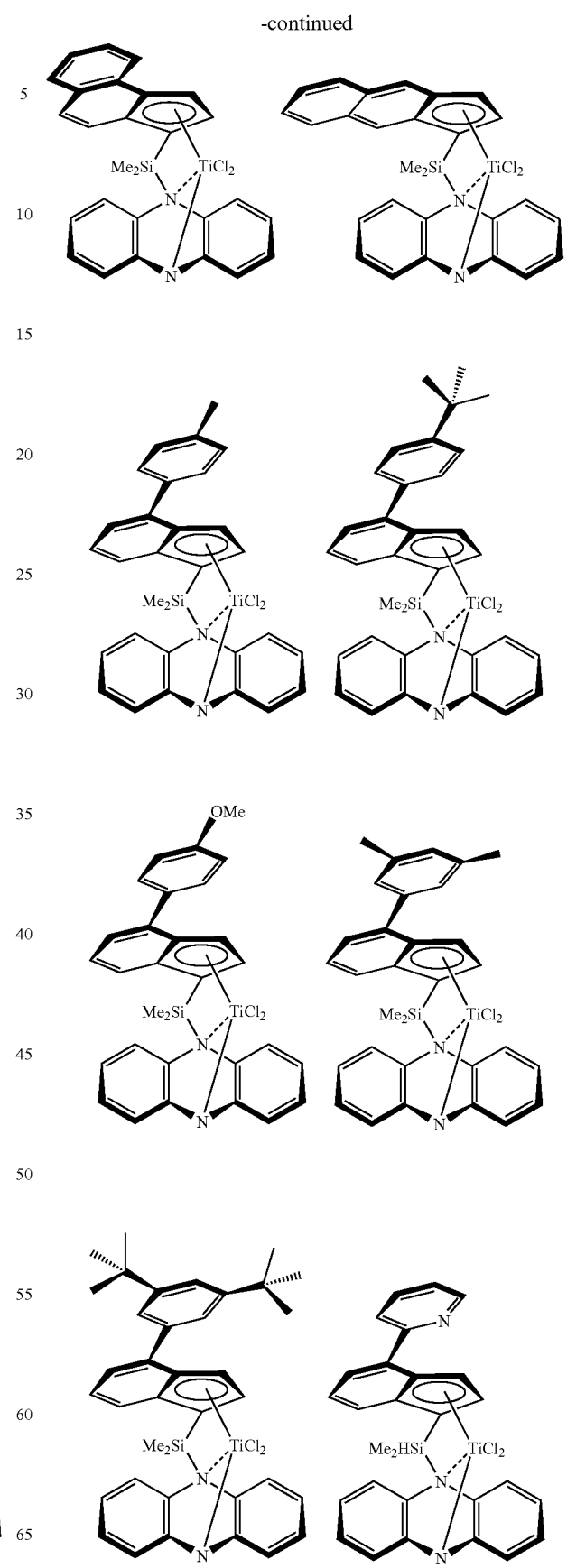

-continued
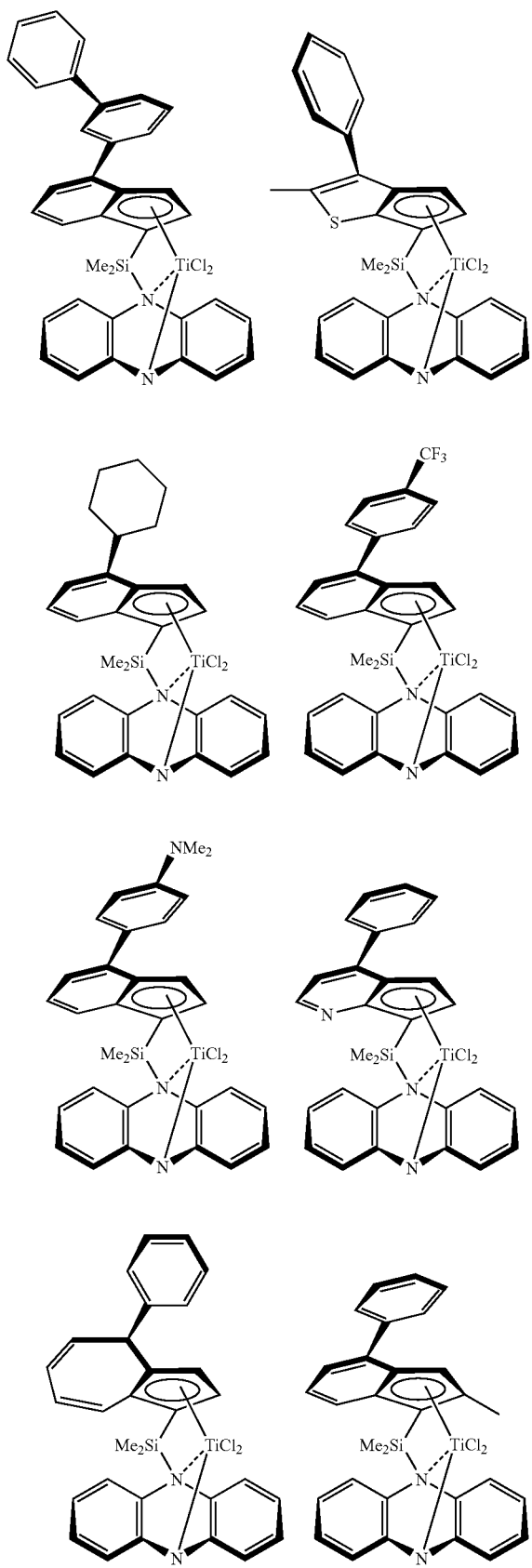
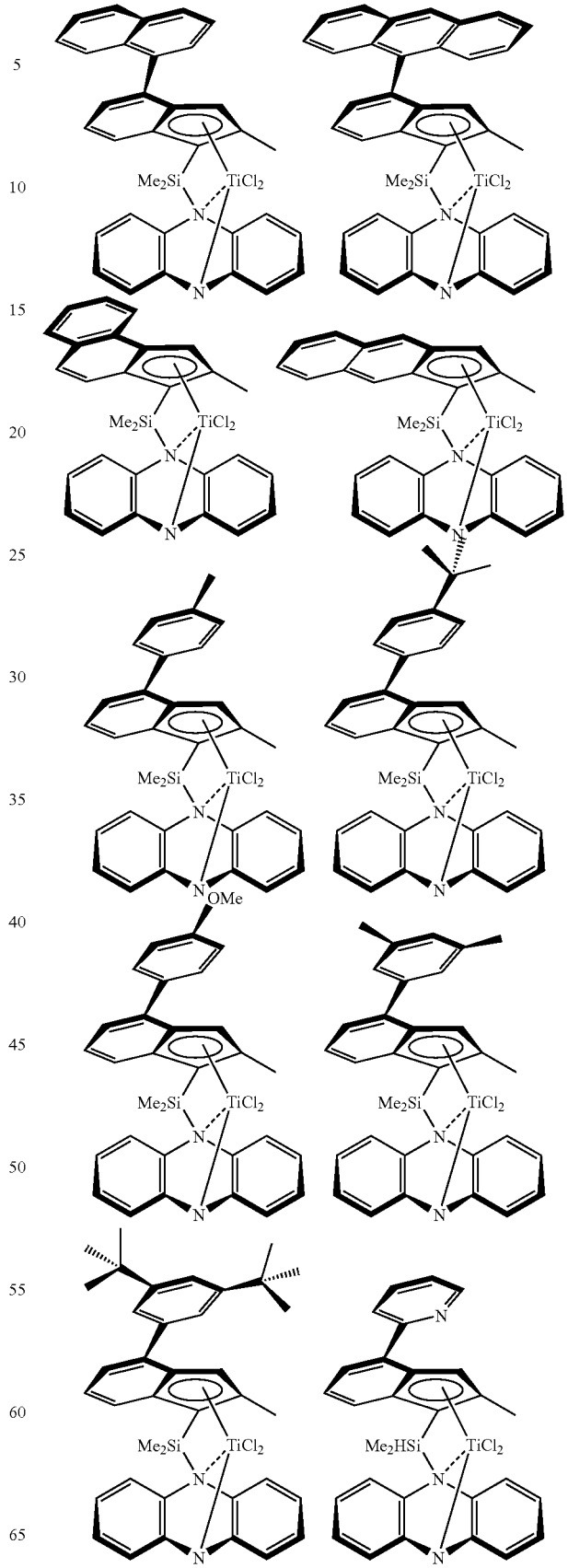

-continued
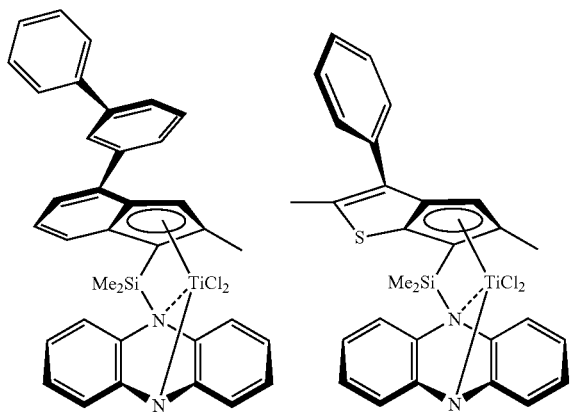
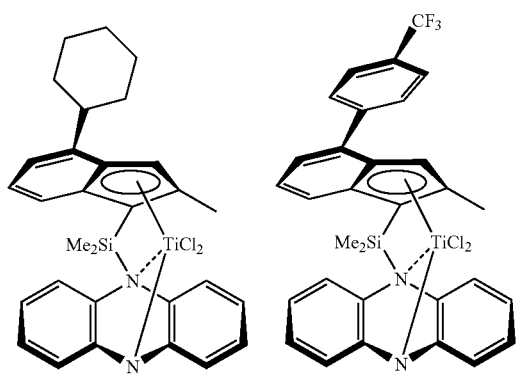
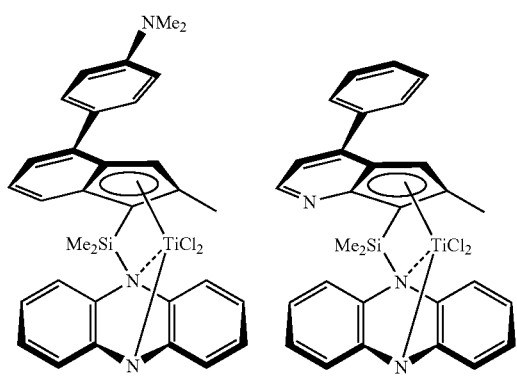
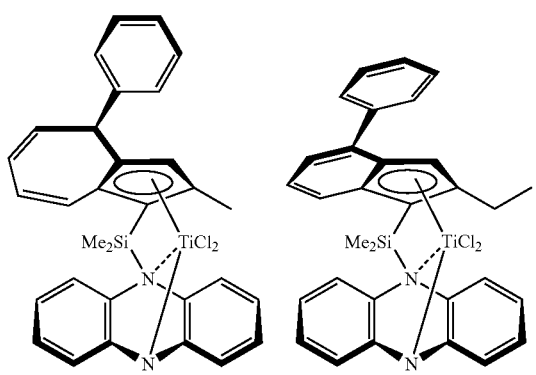
-continued
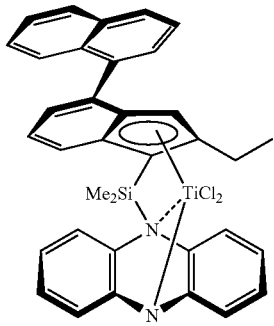
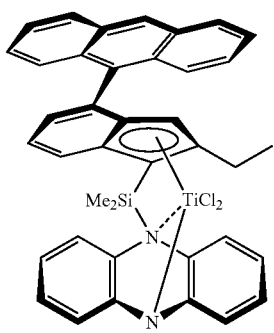
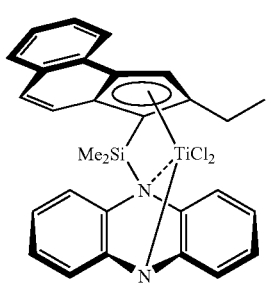
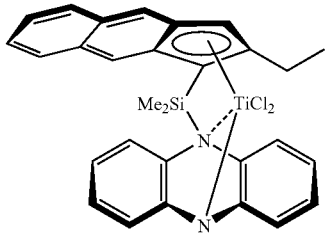
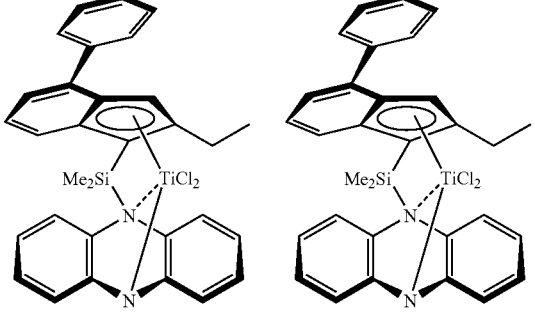

-continued
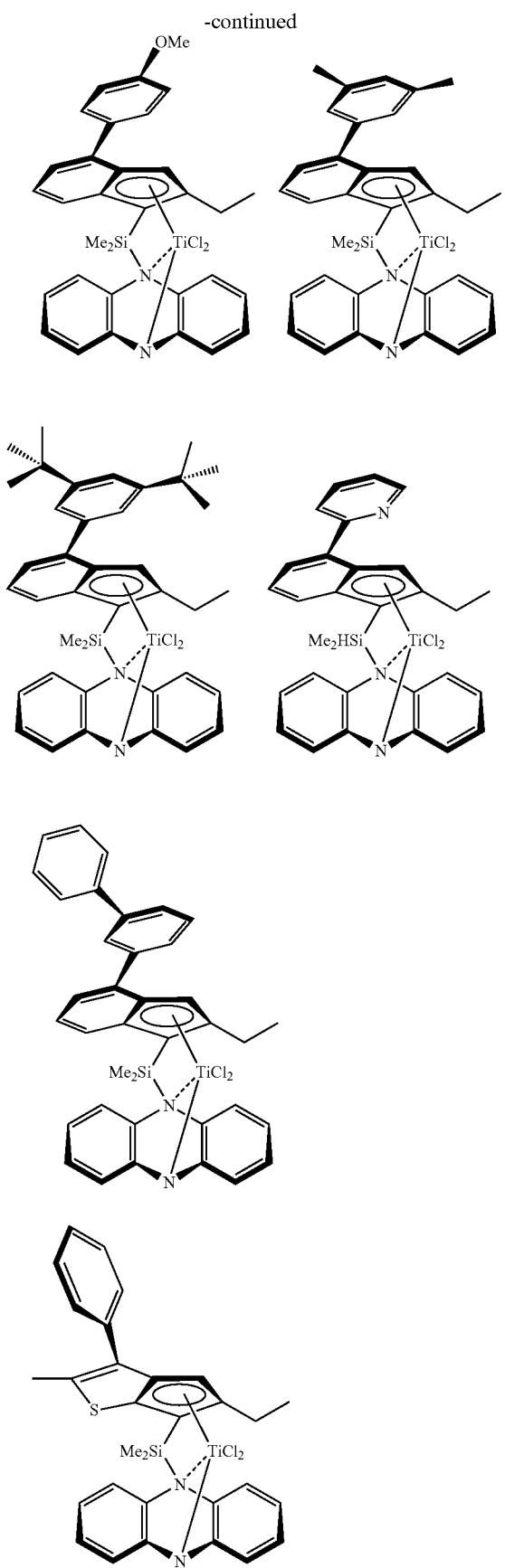
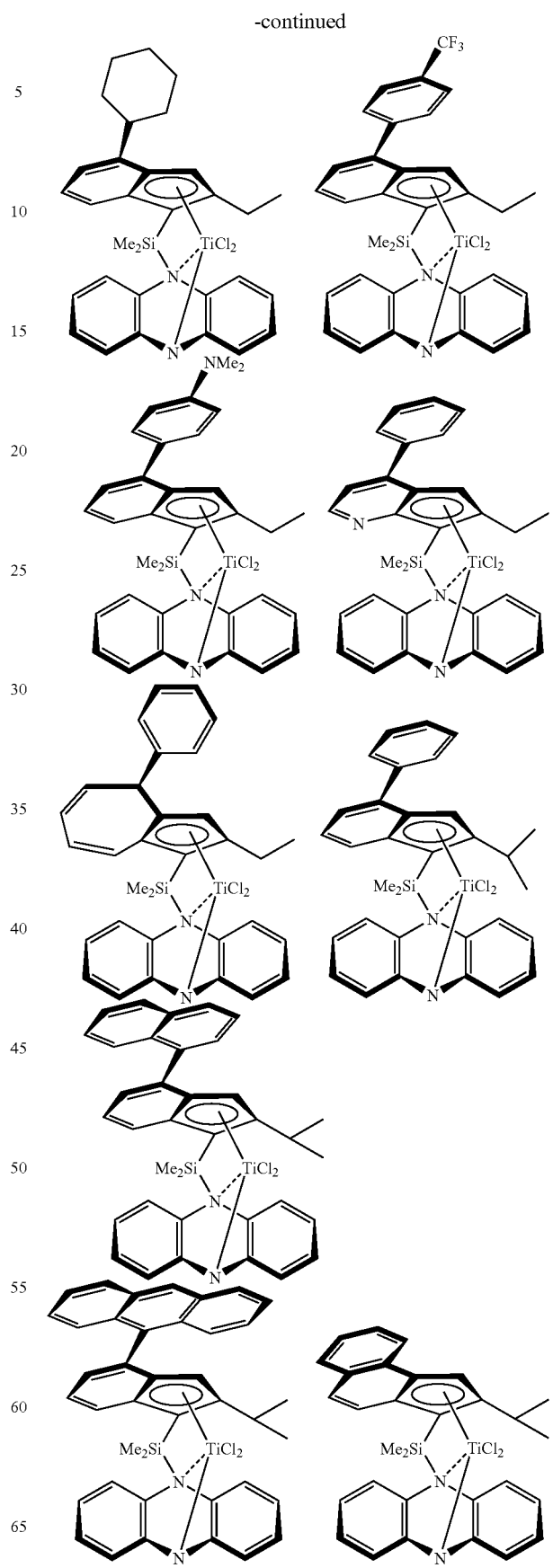

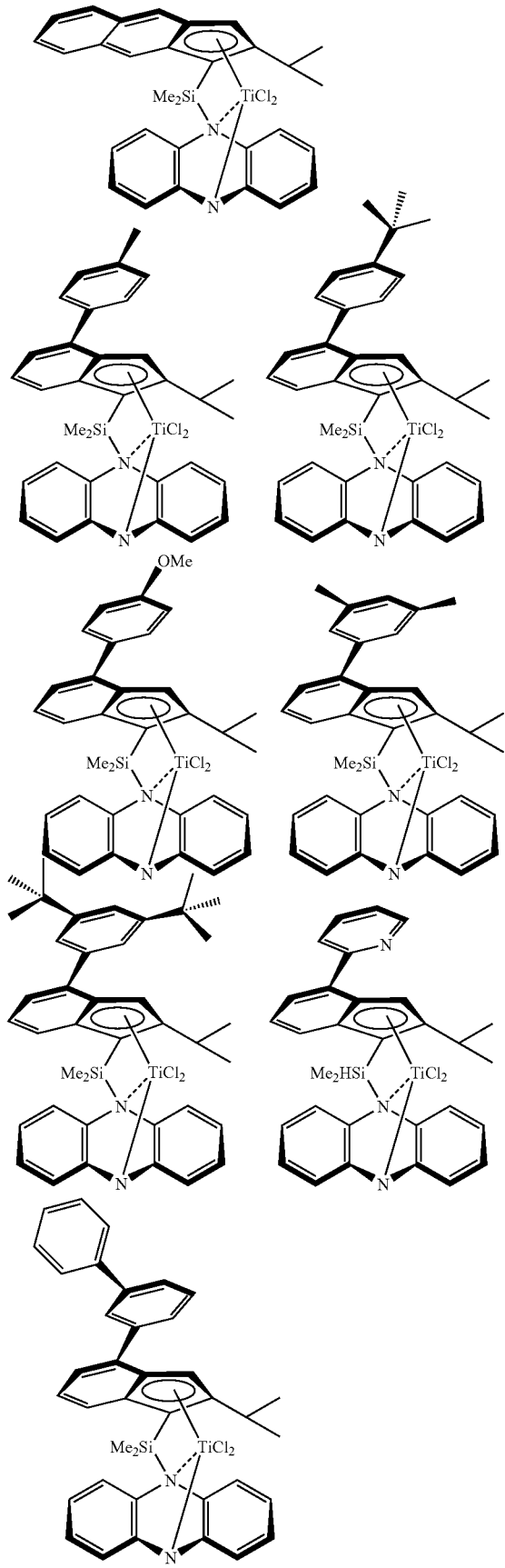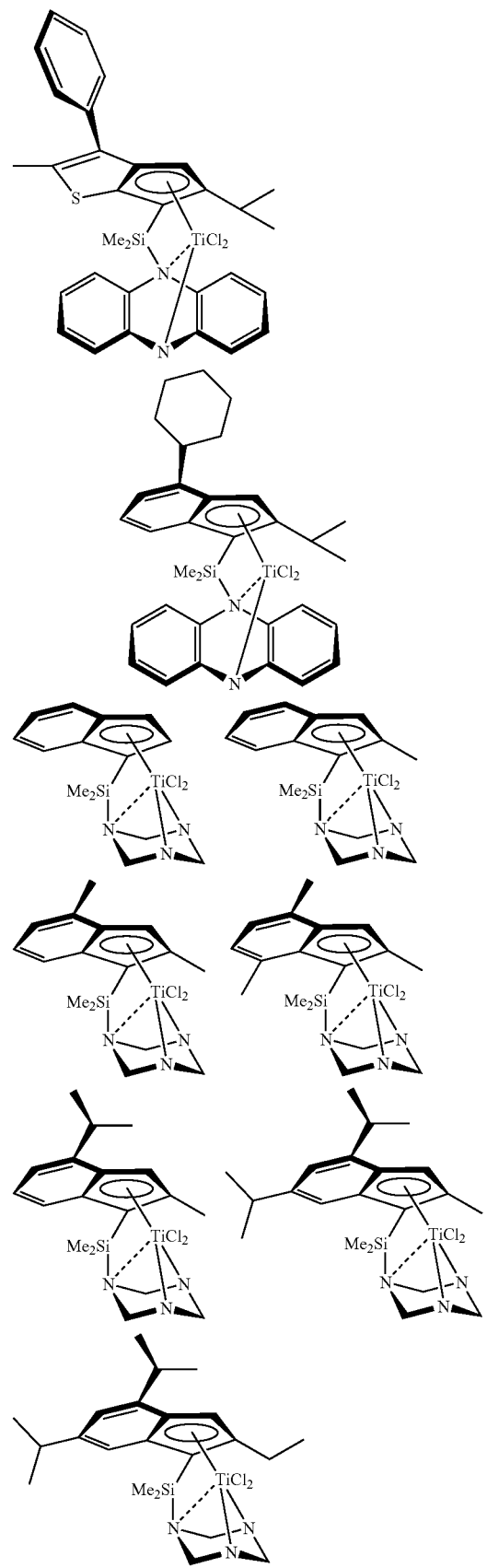

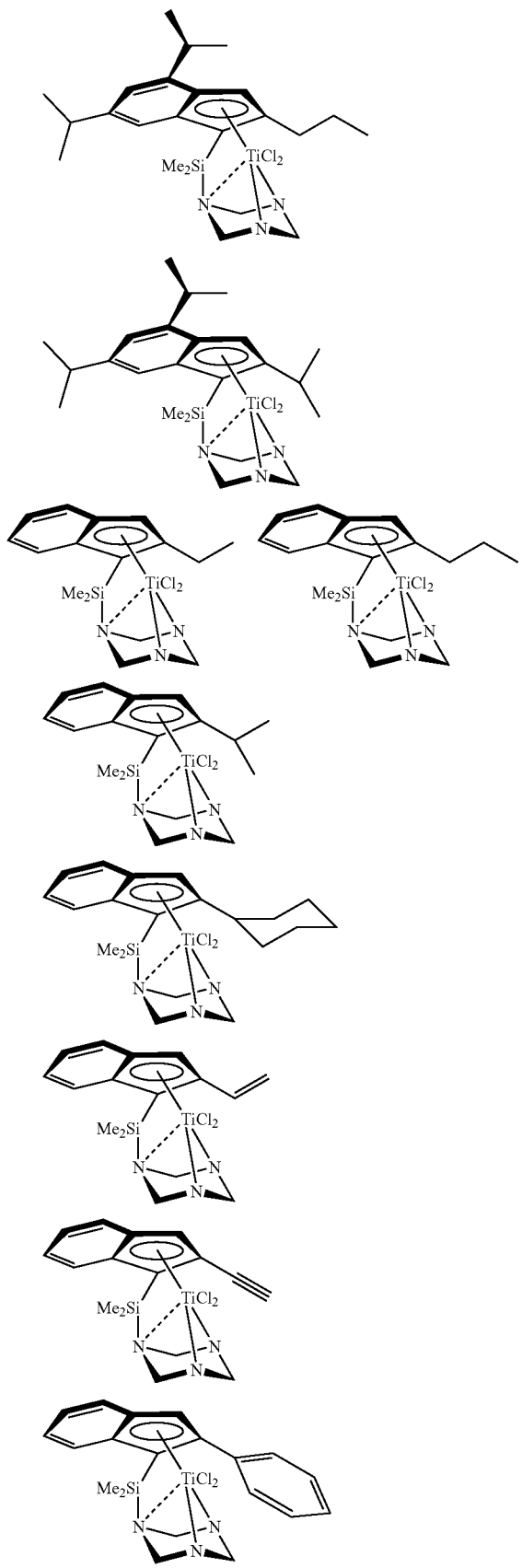
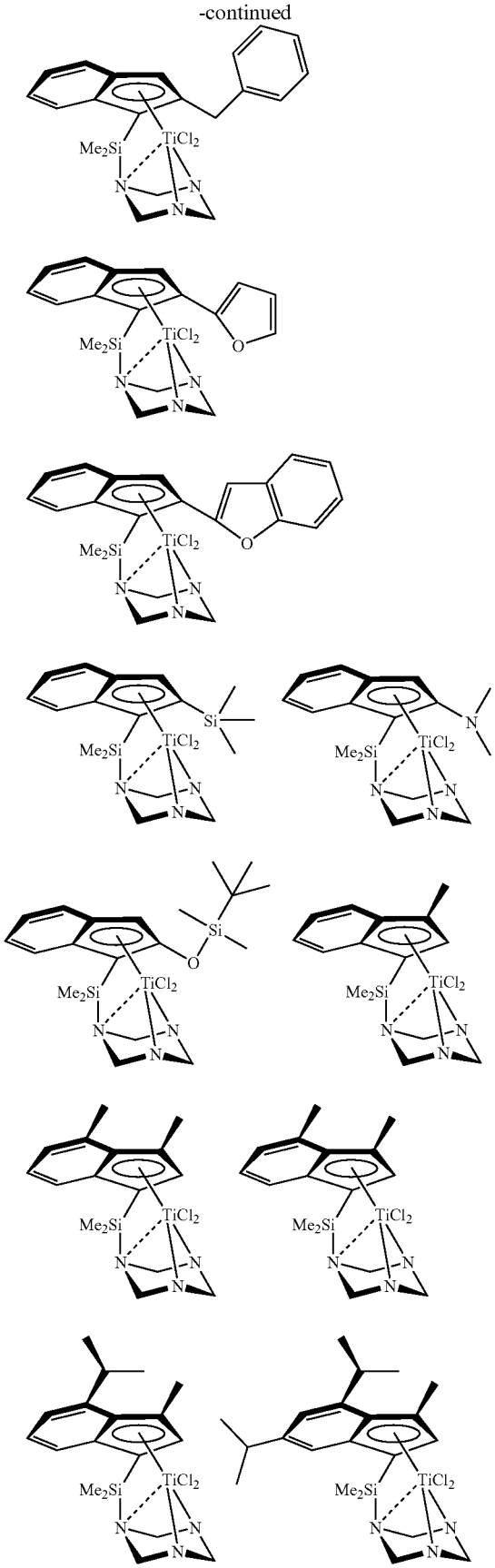

-continued
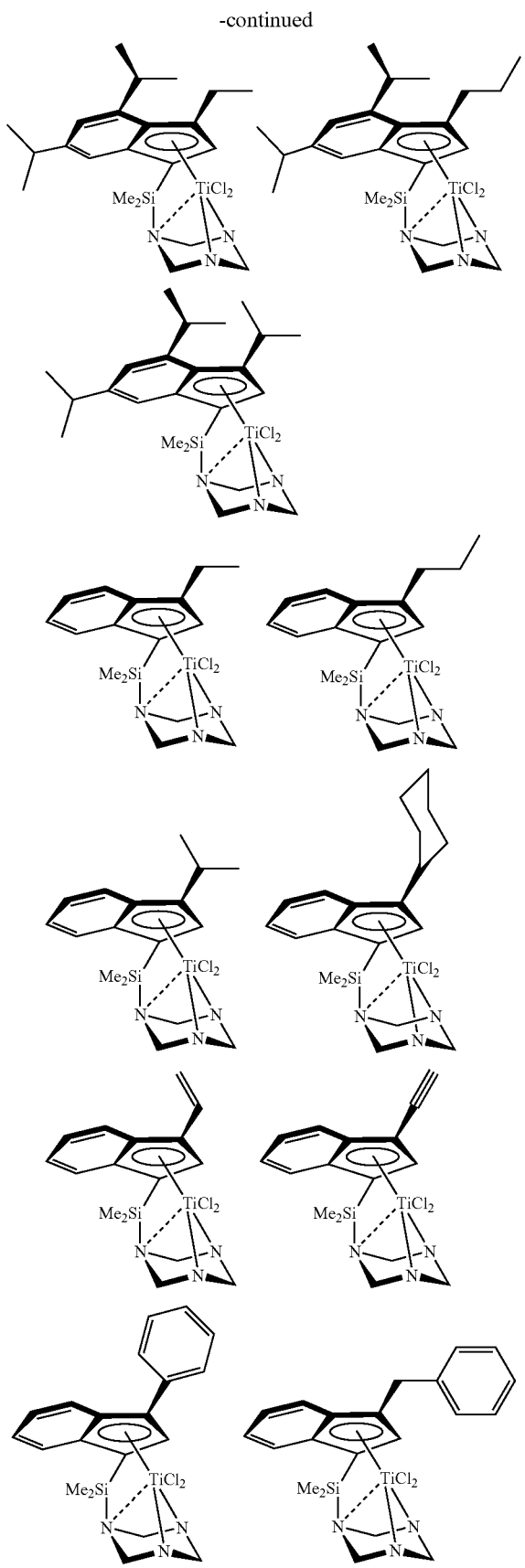
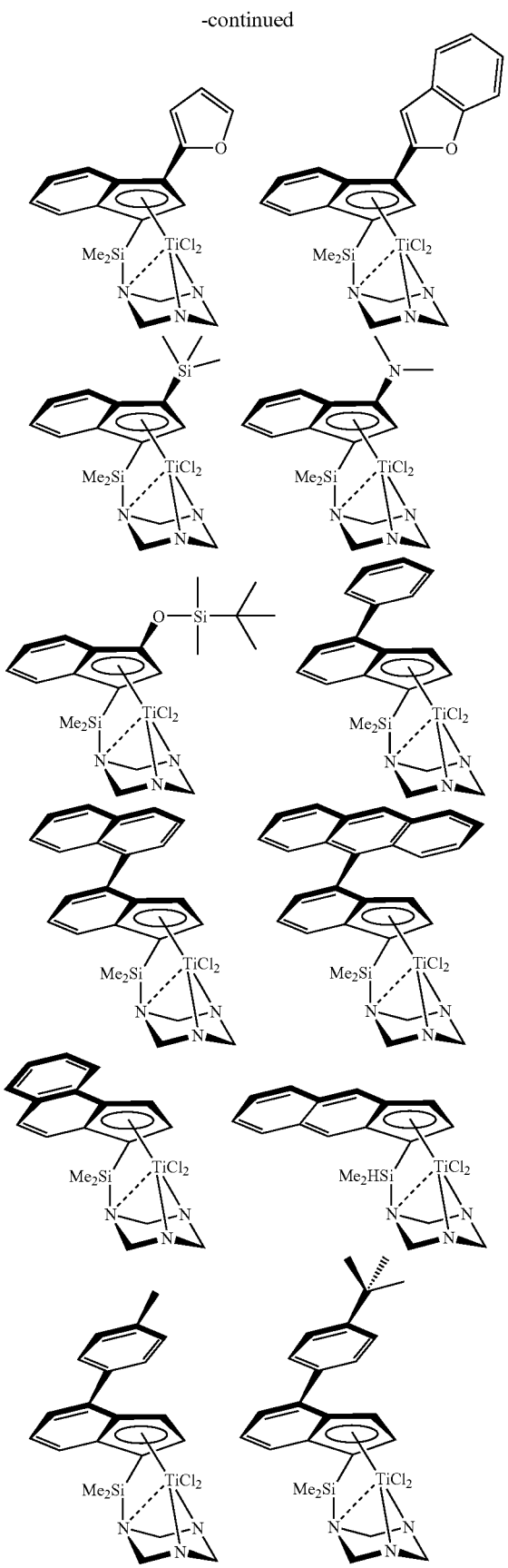

-continued
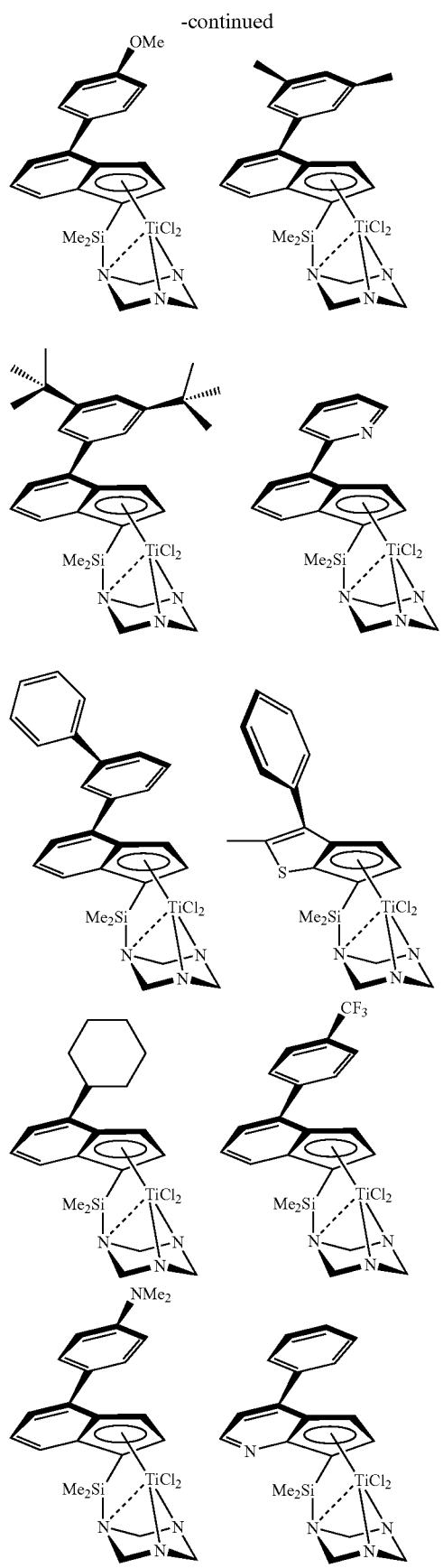
-continued
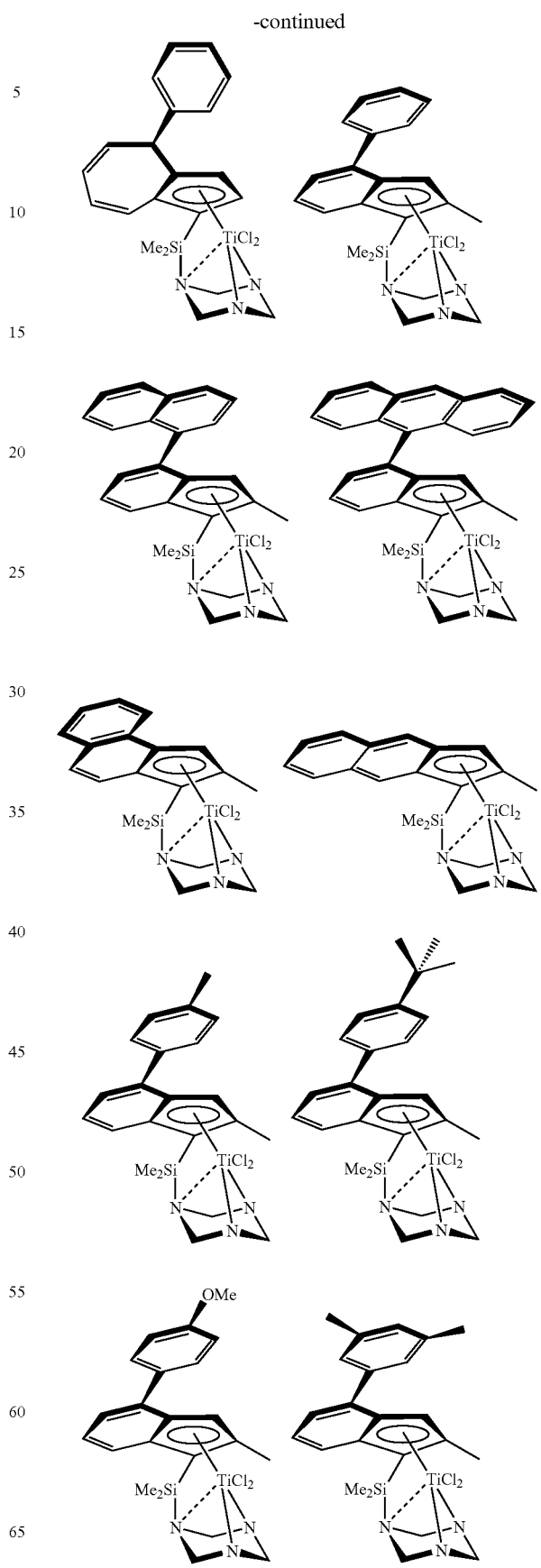

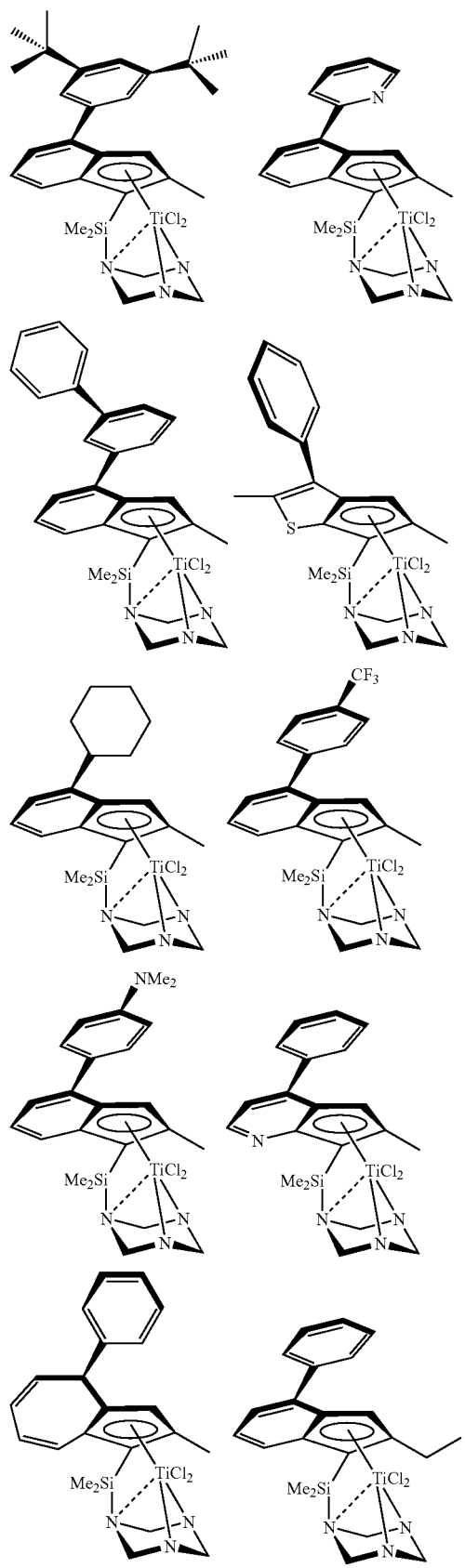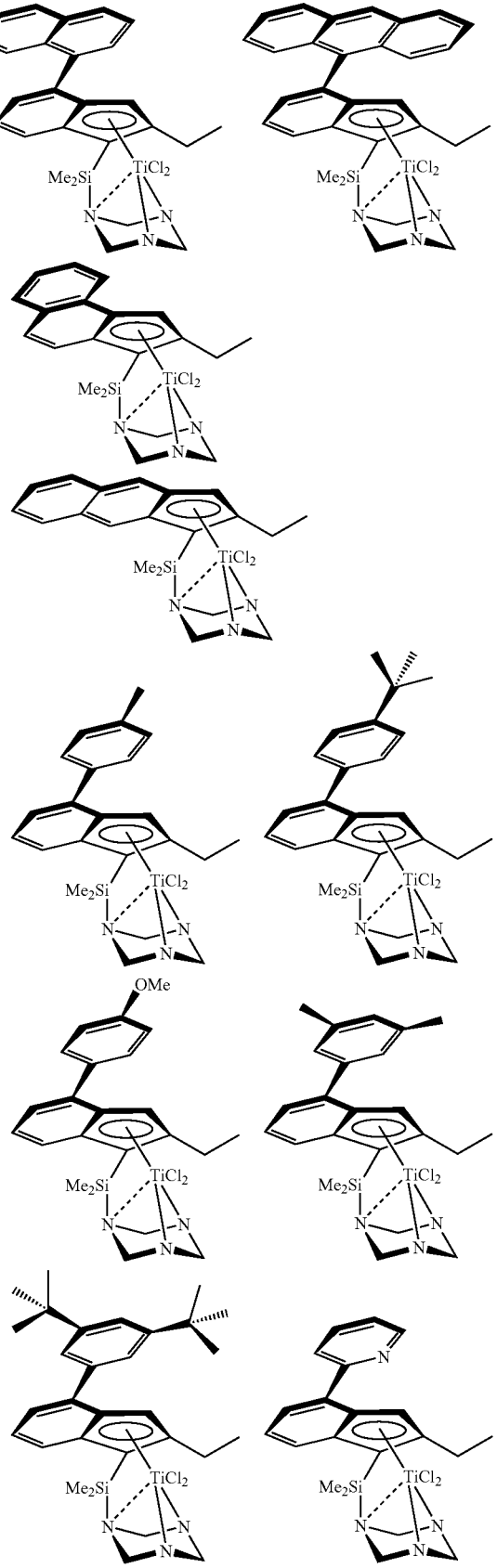

-continued
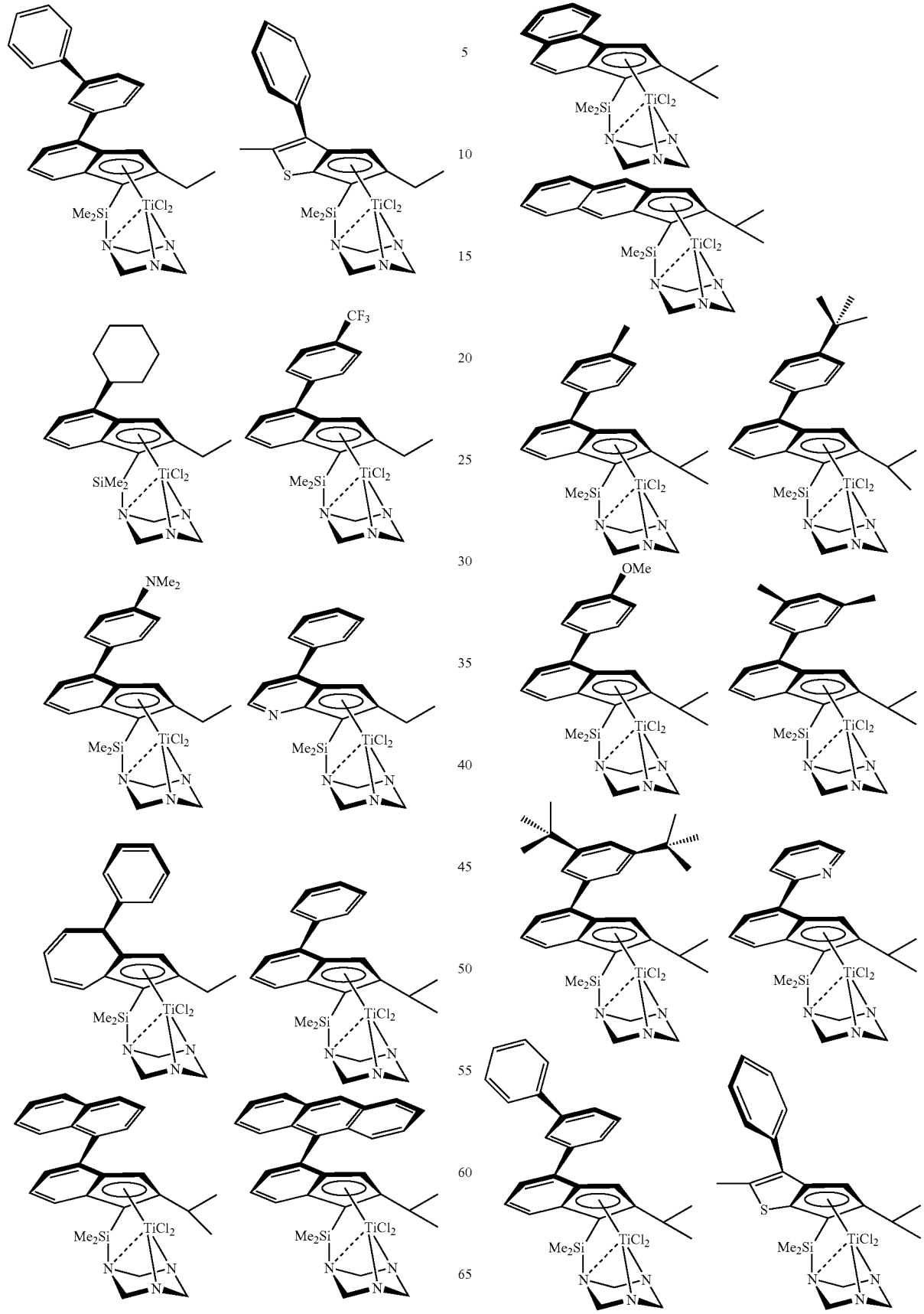

-continued
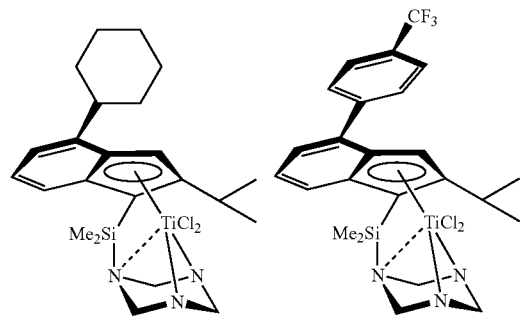
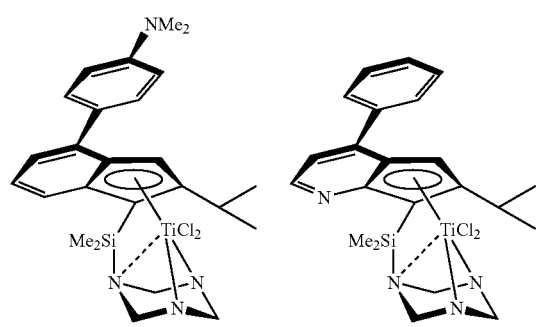
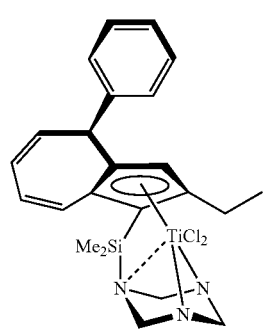
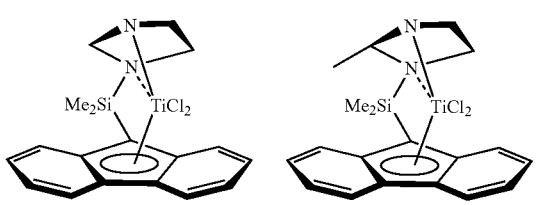
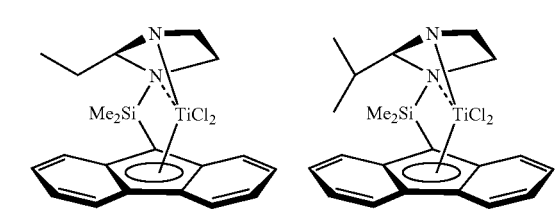
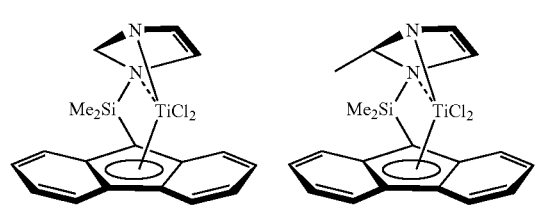
-continued
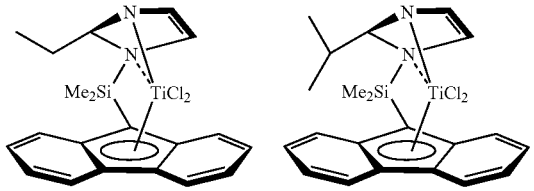
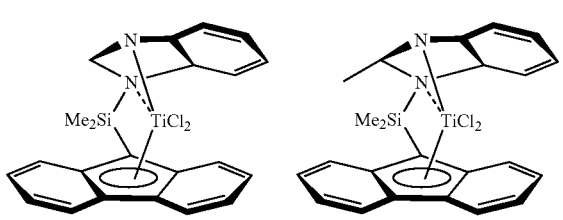
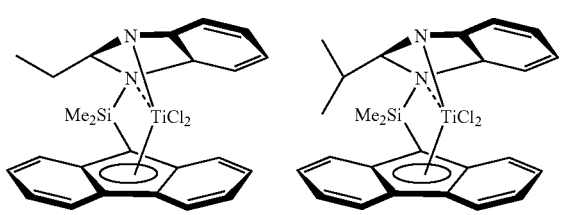
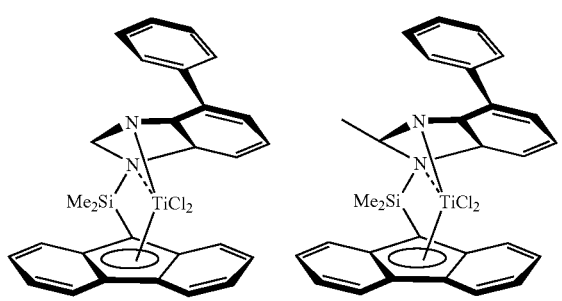
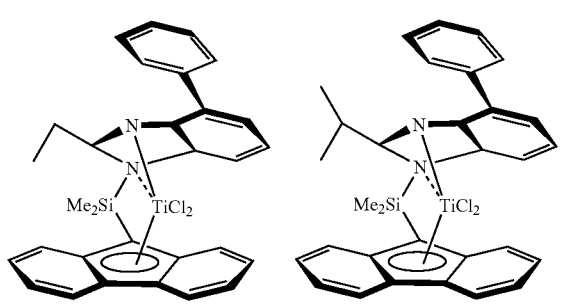
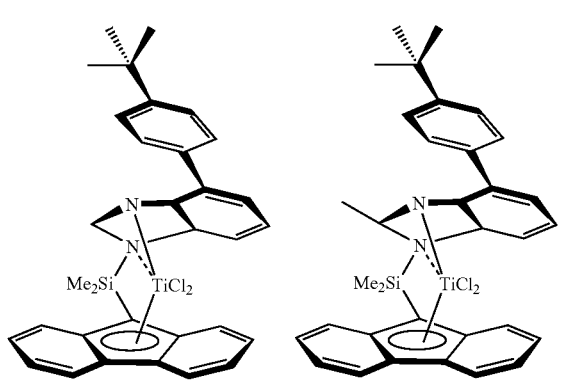

-continued
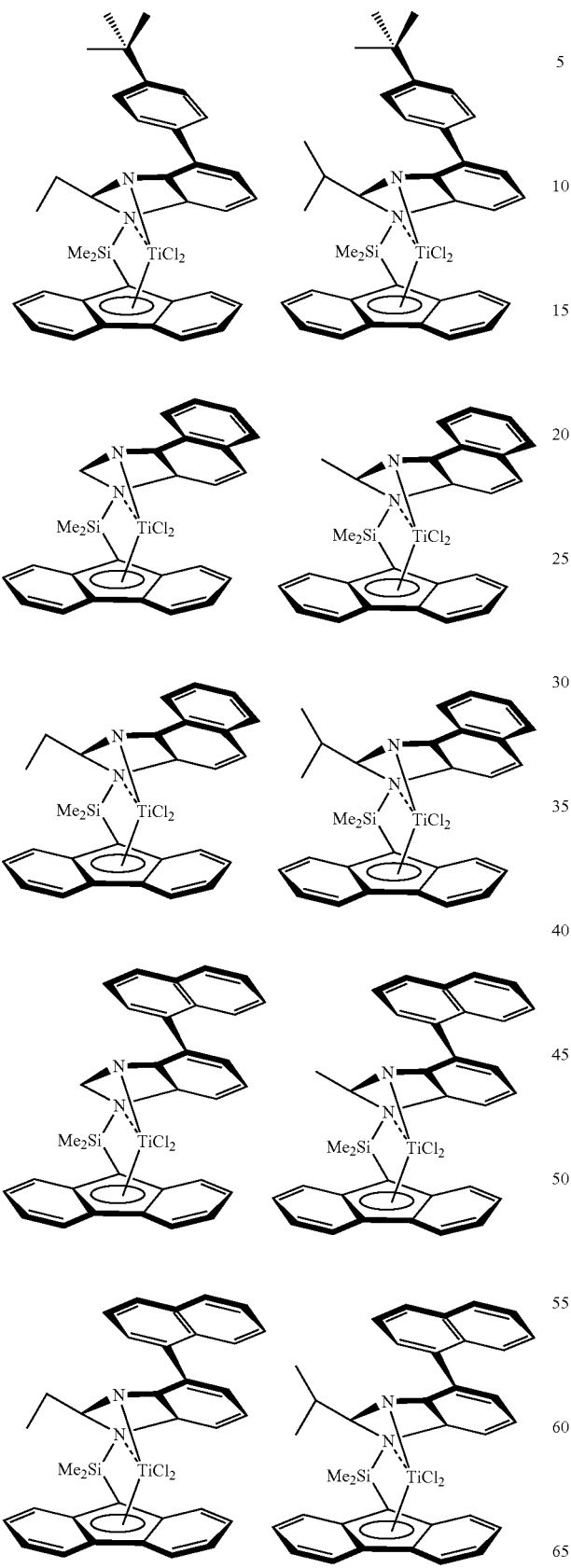
-continued
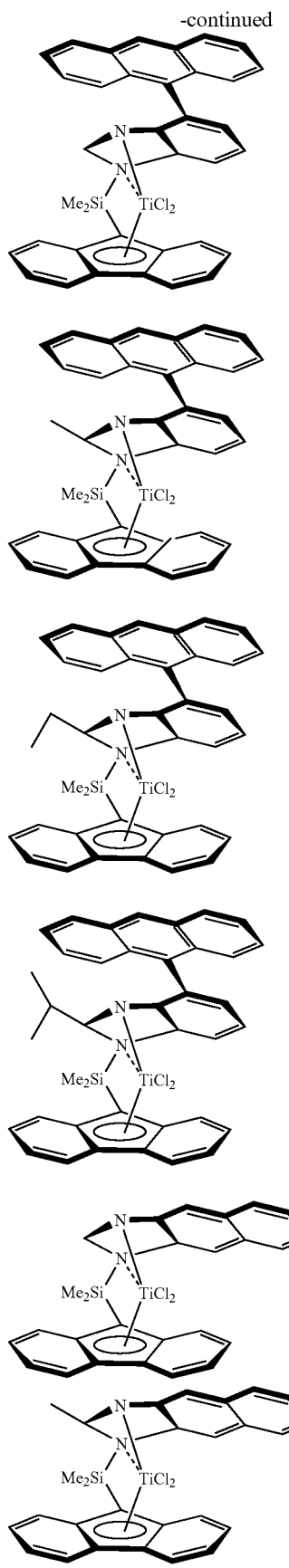

-continued
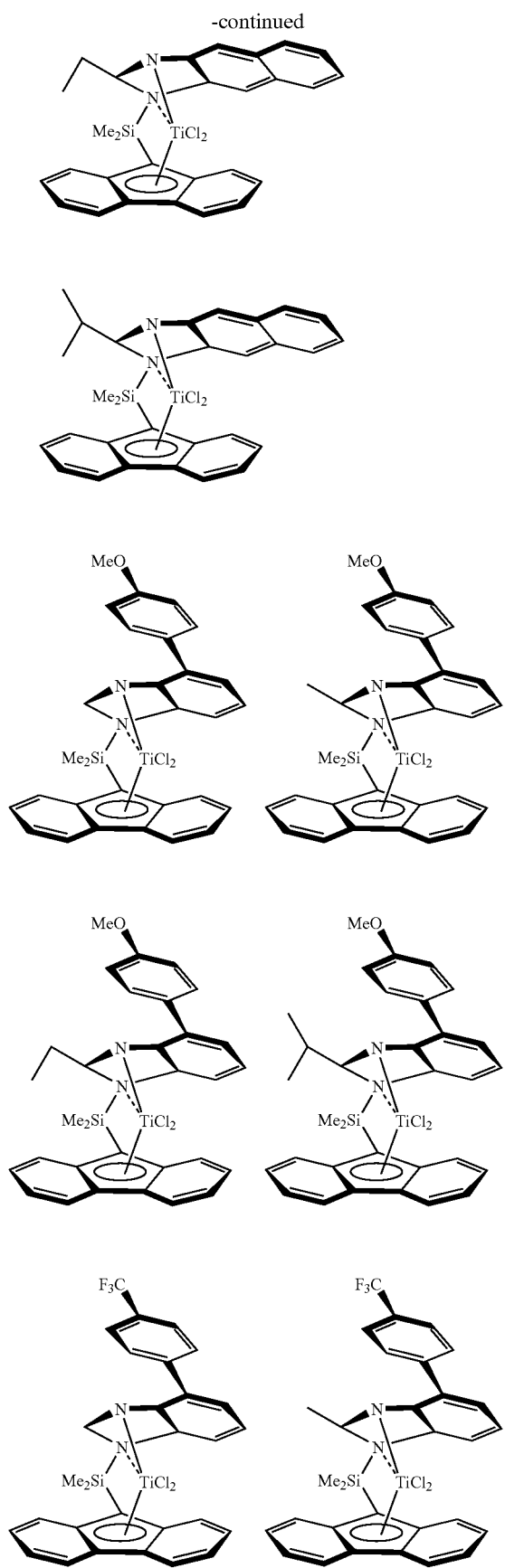
-continued
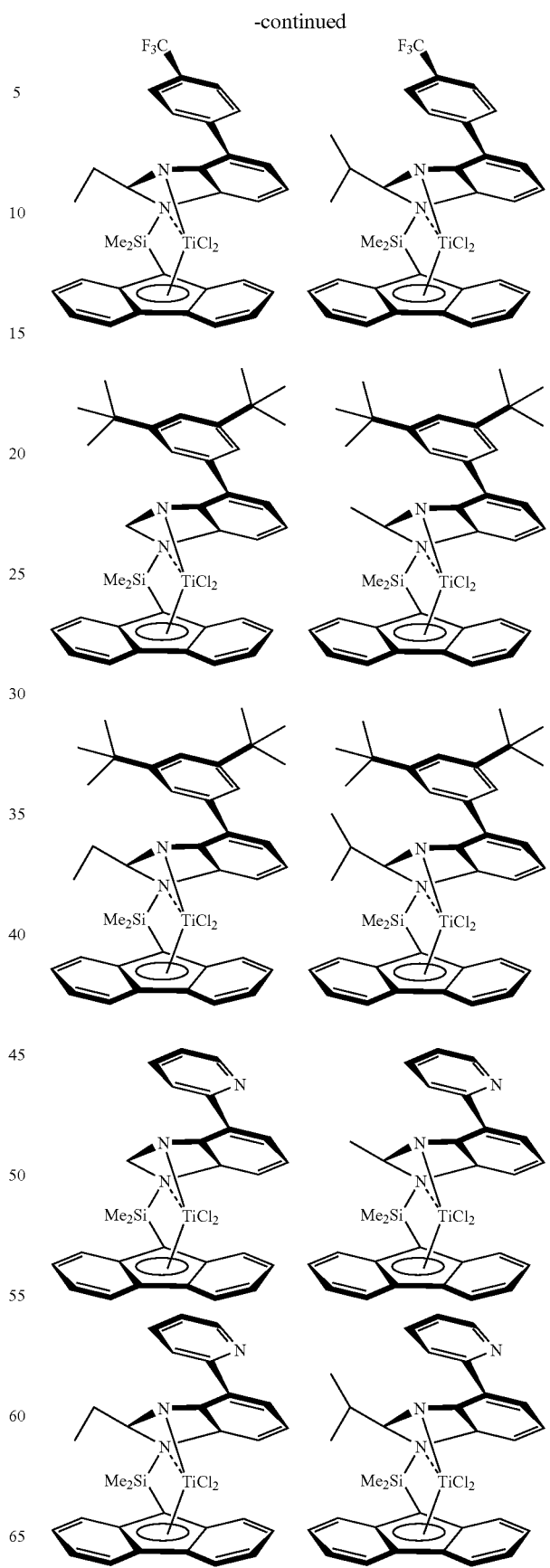

-continued
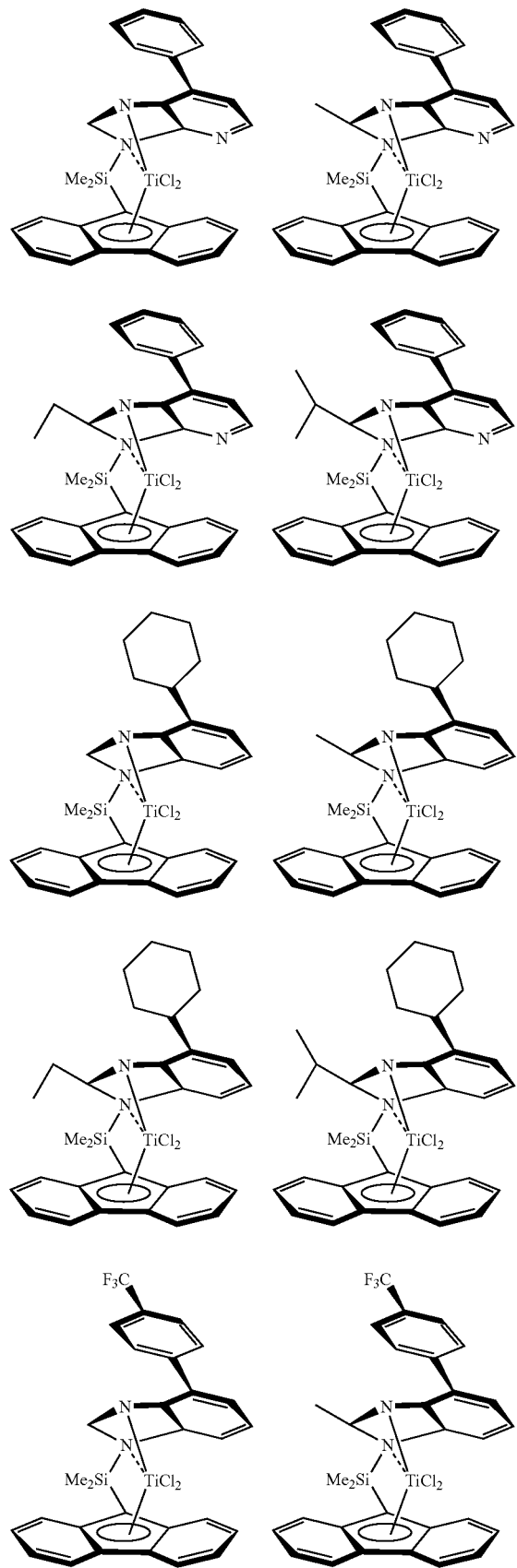
-continued
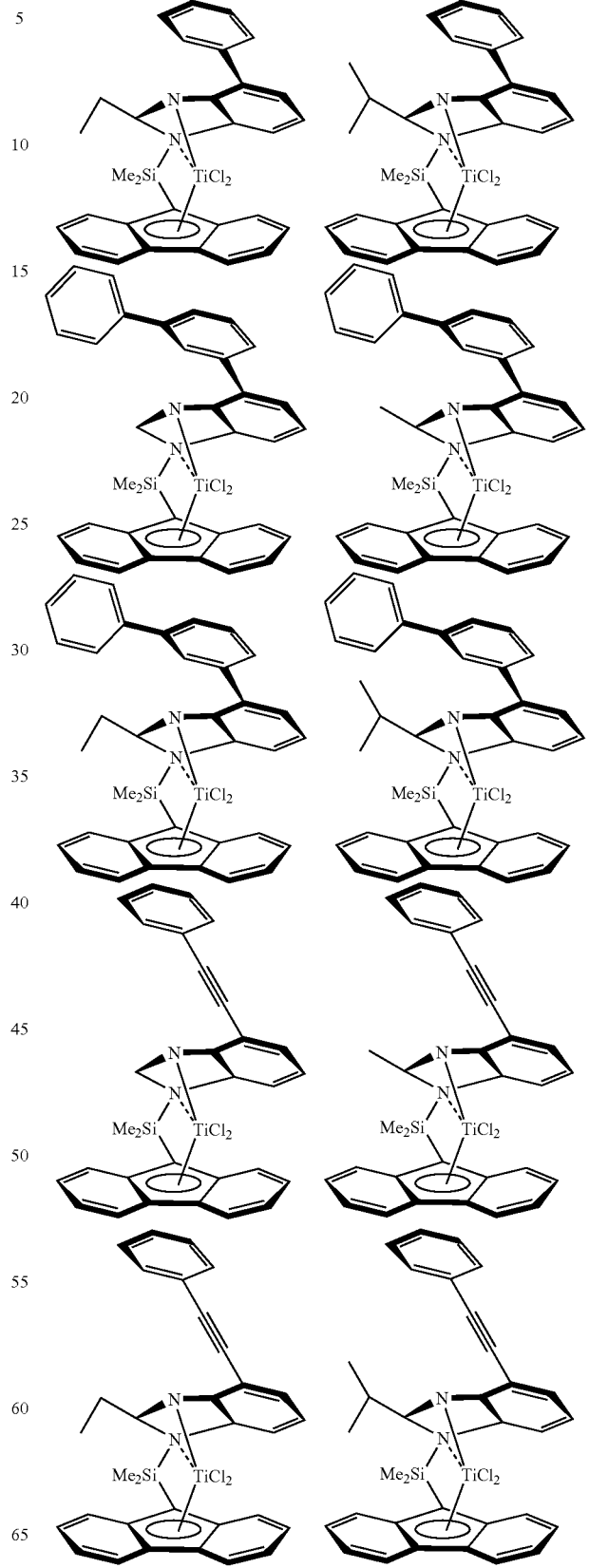

-continued
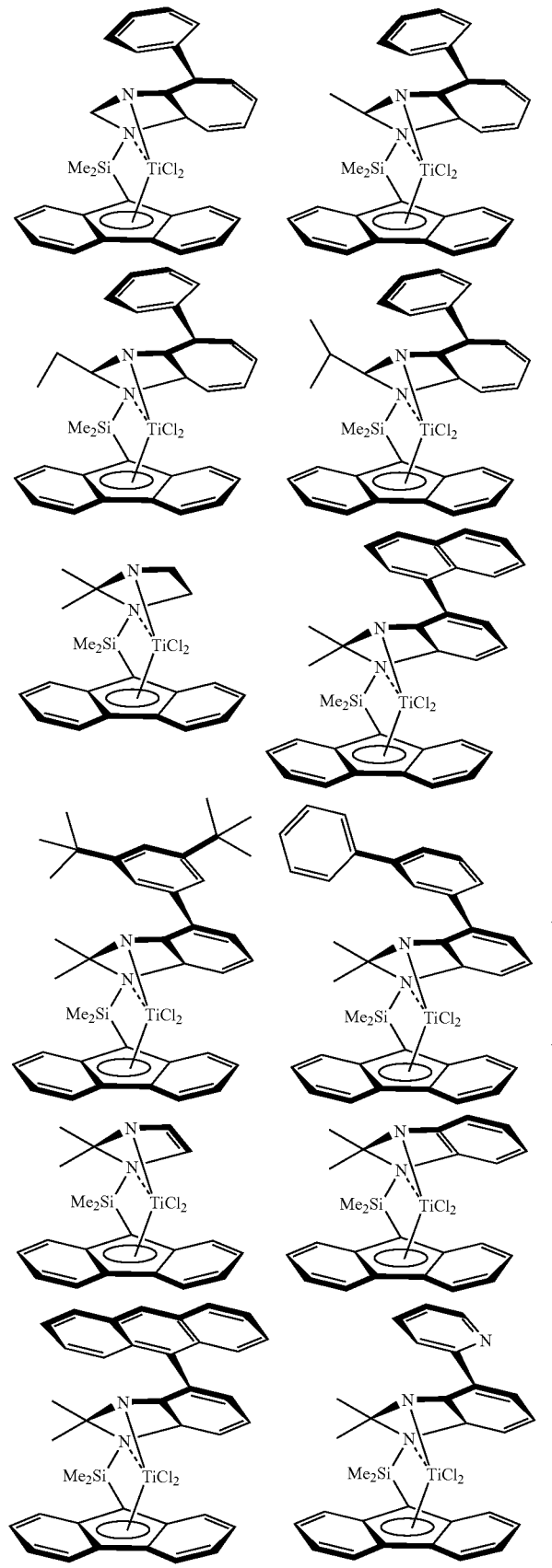
-continued
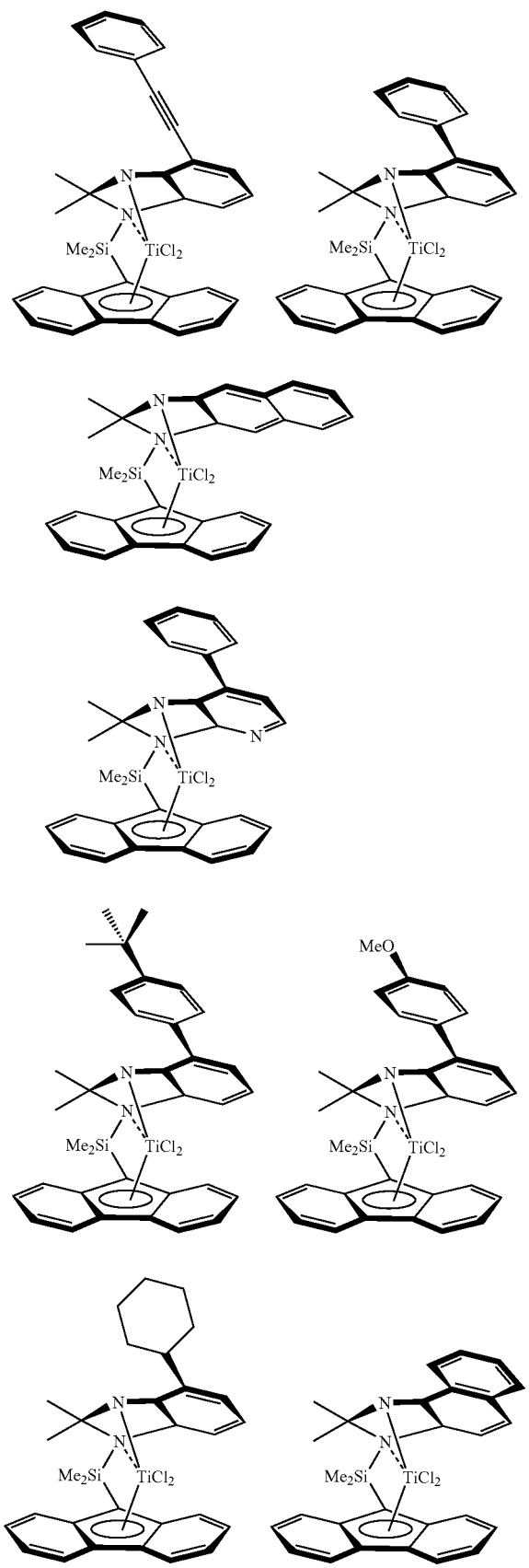

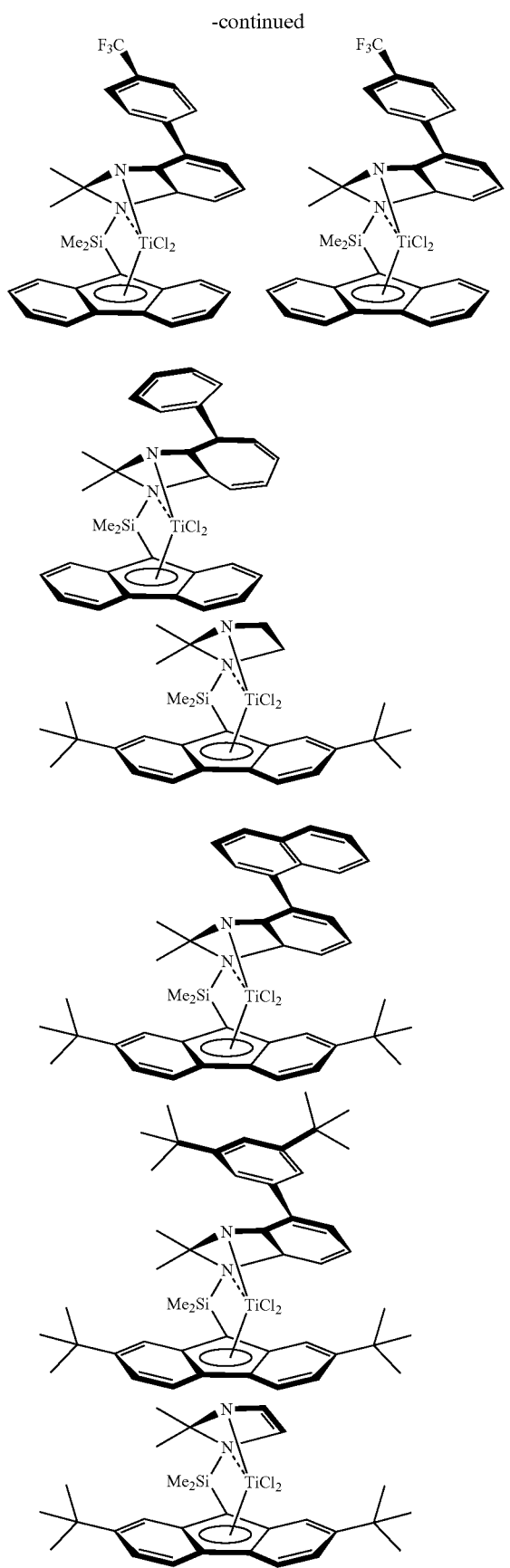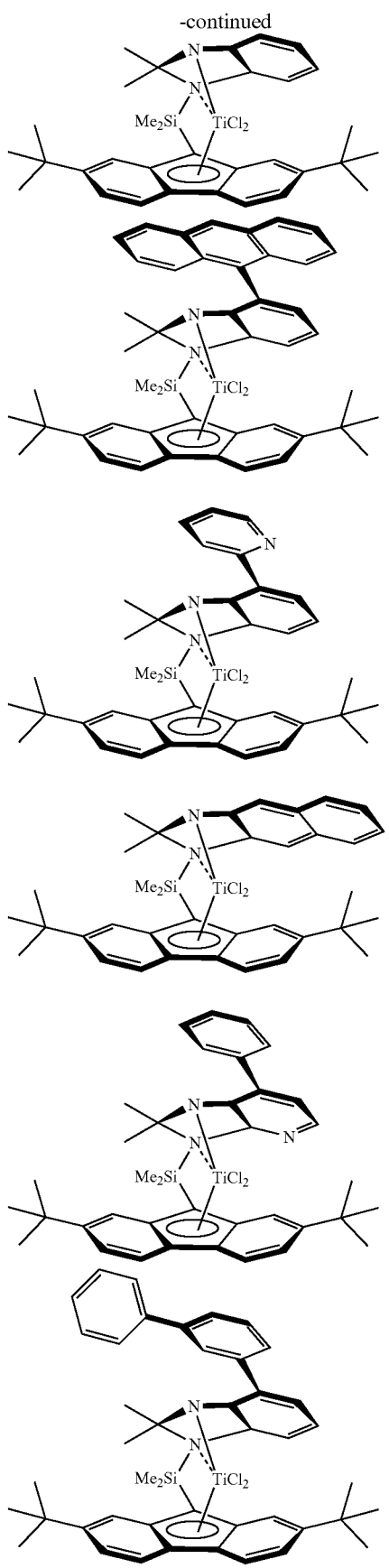

-continued

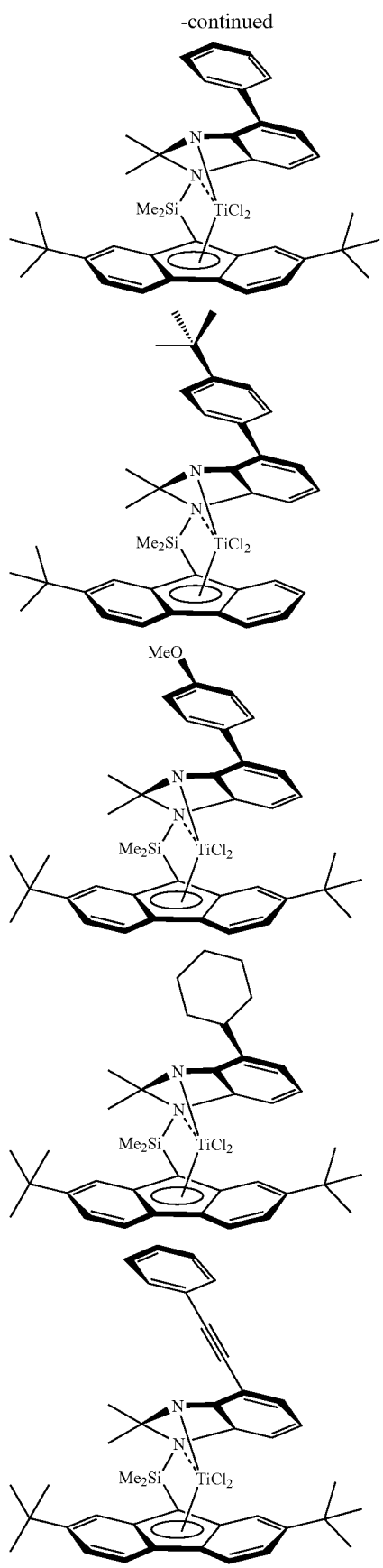

-continued

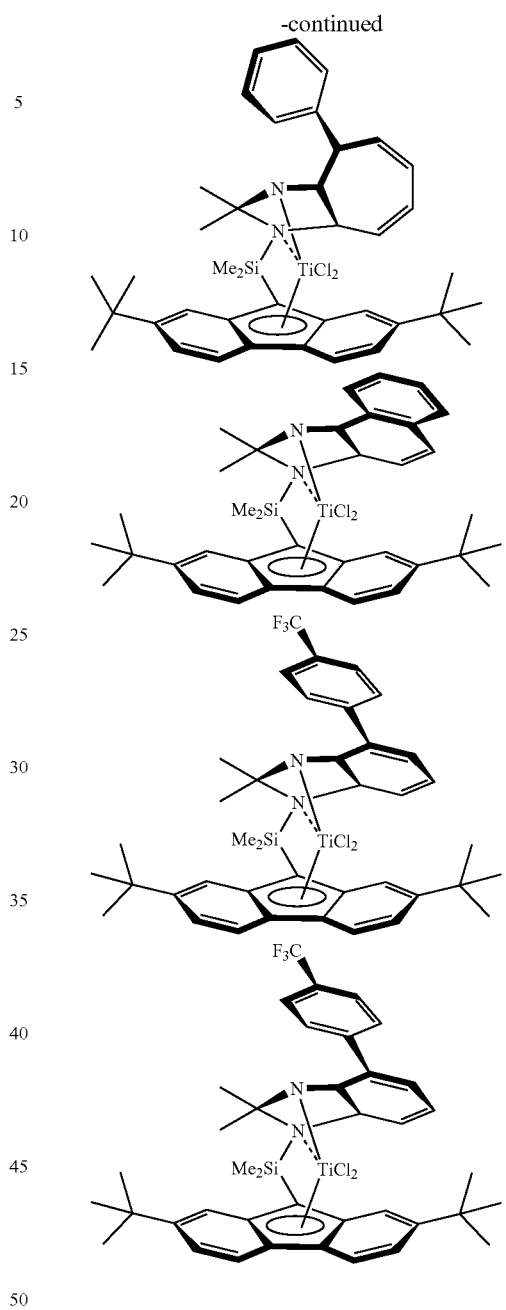

and also the corresponding zirconium and hafnium complexes and the compounds in which a bridge $(Z)_a$ having one of the above meanings has replaced the $SiMe_2$ bridge and the compounds in which X has one of the above meanings, e.g. methyl.

The transition metal complexes of the invention can be synthesized as follows: The ligands can, for example, be obtained by reaction of dimethylchloro-substituted indenes with bisamines or alkali metal salts of the bisamines with dimethylchloro-substituted indenes, or lithiated indenes with dimethylchloro-substituted mono-protected bisamines with subsequent elimination of the protective group. Reaction of the ligands with bases, e.g. butyllithium, followed by reaction with transition metal halides, e.g. titanium tetrachloride, or reaction of the ligand with dialkylmetal dihalides gives the target complexes.

The corresponding metal-alkyl compounds can be obtained either by reaction of the ligand with tetralkyl transition metal compounds, or by reaction of the ligand with a base, e.g. butyllithium, followed by reaction with dialkylmetal dihalides, e.g. dimethyltitanium dichloride, or by reaction of the bishalo complex with alkylating reagents, e.g. Grignard compounds, lithium alkyls or aluminium alkyls.

The present invention also provides a catalyst system comprising the novel chemical compound of the formulae Ia or Ib.

The novel metal complexes of the formulae Ia and Ib are particularly useful as constituents of catalyst systems for preparing polyolefins by polymerization of at least one olefin in the -presence of a catalyst comprising at least one cocatalyst and at least one metal complex of the formula Ia or Ib.

The cocatalyst which together with a novel transition metal complex of the formula Ia or Ib forms the catalyst system comprises at least one compound such as an aluminoxane or a Lewis acid or an ionic compound which reacts with a metal complex to convert it into a cationic compound.

As aluminoxane, preference is given to using a compound of the general formula (III)

$$(R\ AlO)_n \quad (III).$$

Further suitable aluminoxanes can, for example, be cyclic as in the formula (IV)

(IV)

or linear as in the formula (V)

(V)

or of the cluster type as in the formula (VI)

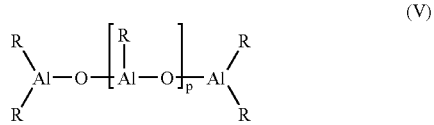

(VI)

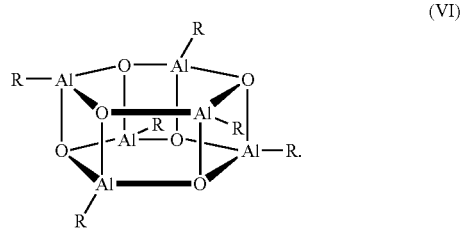

Such aluminoxanes are described, for example, in JACS 117 (1995), 6465–74, Organometallics 13 (1994), 2957–2969.

The radicals R in the formulae (III), (IV), (V) and (VI) can be identical or different and can each be a $C_1$–$C_{20}$-hydrocarbon group such as a $C_1$–$C_6$-alkyl group, a $C_6$–$C_{18}$-aryl group, benzyl or hydrogen and p is an integer from 2 to 50, preferably from 10 to 35. The radicals R are preferably identical and are each methyl, isobutyl, n-butyl, phenyl or benzyl, particularly preferably methyl.

If the radicals R are different, they are preferably methyl and hydrogen, methyl and isobutyl or methyl and n-butyl, with hydrogen or isobutyl or n-butyl preferably being present in a proportion of 0.01–40% (number of radicals R).

The aluminoxane can be prepared in various ways by known methods. One of the methods is, for example, to react an aluminium-hydrocarbon compound and/or a hydridoaluminium-hydrocarbon compound with water (gaseous, solid, liquid or bound, for example as water of crystallization) in an inert solvent (e.g. toluene). To prepare an aluminoxane having different alkyl groups R, two different trialkylaluminiums ($AlR_3$+$AlR'_3$) corresponding to the desired composition and reactivity are reacted with water (cf. S. Pasynkiewicz, Polyhedron 9 (1990) 429 and EP-A-0,302,424).

Regardless of the way in which they are prepared, all aluminoxane solutions have a varying content of unreacted aluminium starting compound which is present in free form or as adduct.

As Lewis acid, preference is given to using at least one organoboron or organoaluminium compound containing $C_1$–$C_{20}$ groups such as branched or unbranched alkyl or haloalkyl, e.g. methyl, propyl, isopropyl, isobutyl, trifluoromethyl, unsaturated groups such as aryl or haloaryl, e.g. phenyl, tolyl, benzyl groups, p-fluorophenyl, 3,5-difluorophenyl, pentachlorophenyl, pentafluorophenyl, 3,4,5-trifluorophenyl and 3,5-di(trifluoromethyl)phenyl.

Examples of Lewis acids are trimethylaluminium, triethylaluminium, triisobutylaluminium, tributylaluminium, trifluoroborane, triphenylborane, tris(4-fluorophenyl)borane, tris(3,5-difluorophenyl)borane, tris(4-fluoromethylphenyl)borane, tris(pentafluorophenyl)borane, tris(tolyl)borane, tris(3,5-dimethylphenyl)borane, tris(3,5-difluorophenyl)borane and/or tris(3,4,5-trifluorophenyl)borane. Particular preference is given to tris(pentafluorophenyl)borane.

As ionic cocatalysts, preference is given to using compounds which contain a noncoordinating anion such as tetrakis(pentafluorophenyl)borate, tetraphenylborate, $SbF_6$—, $CF_3SO_3$—or $ClO_4$—. Cationic counterions used are protonated Lewis bases such as methylamine, aniline, N,N-dimethylbenzylamine and derivatives, N,N-dimethylcyclohexylamine and derivatives, dimethylamine, diethylamine, N-methylaniline, diphenylamine, N,N-dimethylaniline, trimethylamine, triethylamine, tri-n-butylamine, methyldiphenylamine, pyridine, p-bromo-N,N-dimethylaniline, p-nitro-N,N-dimethylaniline, triethylphosphine, triphenylphosphine, diphenylphosphine, tetrahydrothiophene or triphenylcarbenium.

Examples of such ionic compounds are
triethylammonium tetra(phenyl)borate,
tributylammonium tetra(phenyl)borate,
trimethylammonium tetra(tolyl)borate,
tributylammonium tetra(tolyl)borate,
tributylammonium tetra(pentafluorophenyl)borate,
tributylammonium tetra(pentafluorophenyl)aluminate,
tripropylammonium tetra(dimethylphenyl)borate,
tributylammonium tetra(trifluoromethylphenyl)borate,
tributylammonium tetra(4-fluorophenyl)borate,
N,N-dimethylanilinium tetra(phenyl)borate,
N,N-diethylanilinium tetra(phenyl)borate,
N,N-dimethylanilinium tetrakis(pentafluorophenyl)borate,
N,N-dimethylanilinium tetrakis(pentafluorophenyl)aluminate,
N,N-dimethylcyclohexylammonium tetrakis(pentafluorophenyl)borate, N,N-dimethylbenzylammonium tetrakis(pentafluorophenyl)borate,
di(propyl)ammonium tetrakis(pentafluorophenyl)borate,
di(cyclohexyl)ammonium tetrakis(pentafluorophenyl)borate,
triphenylphosphonium tetrakis(phenyl)borate,
triethylphosphonium tetrakis(phenyl)borate,
diphenylphosphonium tetrakis(phenyl)borate,
tri(methylphenyl)phosphonium tetrakis(phenyl)borate,
tri(dimethylphenyl)phosphonium tetrakis(phenyl)borate,
triphenylcarbenium tetrakis(pentafluorophenyl)borate,
triphenylcarbenium tetrakis(pentafluorophenyl)aluminate,
triphenylcarbenium tetrakis(phenyl)aluminate,
ferrocenium tetrakis(pentafluorophenyl)borate and/or
ferrocenium tetrakis(pentafluorophenyl)aluminate.

Preference is given to triphenylcarbenium tetrakis(pentafluorophenyl)borate and/or N,N-dimethylanilinium tetrakis(pentafluorophenyl)borate.

It is also possible to use mixtures of at least one Lewis acid and at least one ionic compound.

Cocatalyst components which are likewise of importance are borane or carborane compounds such as
7,8-dicarbaundecaborane(13),
undecahydrido-7,8-dimethyl-7,8-dicarbaundecaborane,
dodecahydrido-1-phenyl-1,3-dicarbanonaborane,
tri(butyl)ammonium undecahydrido-8-ethyl-7,9-dicarbaundecaborate,
4-carbanonaborane(14), bis(tri(butyl)ammonium) nonaborate,
bis(tri(butyl)ammonium) undecaborate,
bis(tri(butyl)ammonium) dodecaborate,
bis(tri(butyl)ammonium) decachlorodecaborate,
tri(butyl)ammonium 1-carbadecaborate,
tri(butyl)ammonium 1-carbadodecaborate,
tri(butyl)ammonium 1-trimethylsilyl-1-carbadecaborate,
tri(butyl)ammonium bis(nonahydrido-1,3-dicarbanonaborato)cobaltate(III),
tri(butyl)ammonium bis(undecahydrido-7,8-dicarbaundecaborato)ferrate(III).

Further cocatalyst systems which are likewise of importance are combinations of at least one of the abovementioned amines and a support with organoelement compounds as are described in WO 99/40129.

Preferred constituents of these cocatalyst systems are the compounds of the formulae (A) and (B),

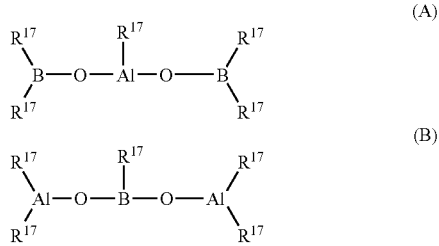

where
$R^{17}$ is a hydrogen atom, a halogen atom, a $C_1$–$C_{40}$ group, in particular $C_1$–$C_{20}$-alkyl, $C_1$–$C_{20}$-haloalkyl, $C_1$–$C_{10}$-alkoxy, $C_6$–$C_{20}$-aryl, $C_6$–$C_{20}$-haloaryl, $C_6$–$C_{20}$-aryloxy, $C_7$–$C_{40}$-arylalkyl, $C_7$–$C_{40}$-haloarylalkyl, $C_7$–$C_{40}$-alkylaryl or $C_7$–$C_{40}$-haloalkylaryl. $R^{17}$ can also be an -OSi$R^{18}{}_3$ group, where the radicals $R^{18}$ are identical or different and are as defined for $R^{17}$.

Further preferred cocatalysts are compounds in general which are formed by reacting at least one compound of the formula (C) and/or (D) and/or (E) with at least one compound of the formula (F),

 (C)

 (D)

 (E)

 (F)

where
$R^{80}$ can be a hydrogen atom or a boron-free $C_1$–$C_{40}$ group such as $C_1$–$C_{20}$-alkyl, $C_6$–$C_{20}$-aryl, $C_7$–$C_{40}$-arylalkyl, $C_7$–$C_{40}$-alkylaryl, and
$R^{17}$ is as defined above,
$X^1$ is an element of main group VI of the Periodic Table of the Elements or an NR group, where R is a hydrogen atom or a $C_1$–$C_{20}$-hydrocarbon radical such as $C_1$–$C_{20}$-alkyl or $C_1$–$C_{20}$-aryl,
D is an element of main group VI of the Periodic Table of the Elements or an NR group, where R is a hydrogen atom or a $C_1$–$C_{20}$-hydrocarbon radical such as $C_1$–$C_{20}$-alkyl or $C_1$–$C_{20}$-aryl,
v is an integer from 0 to 3,
s is an integer from 0 to 3,
h is an integer from 1 to 10,
B is boron,
Al is aluminium.

If desired, the organoelement compounds are combined with an organometallic compound of the formulae III to V and/or VII $[M^{40}R^{19}{}_b]_d$, where $M^{40}$ is an element of main group I, II or III or the Periodic Table of the Elements, the radicals $R^{19}$ are identical or different and are each a hydrogen atom, a halogen atom, a $C_1$–$C_{40}$ group, in particular a $C_1$–$C_{20}$-alkyl, $C_6$–$C_{40}$-aryl, $C_7$–$C_{40}$-arylalkyl or $C_7$–$C_{40}$-alkylaryl group, b is an integer from 1 to 3 and d is an integer from 1 to 4.

Examples of cocatalytically active compounds of the formulae A and B are

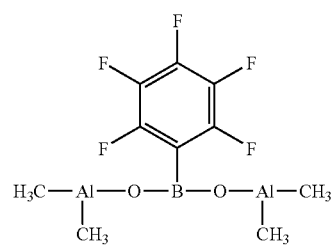

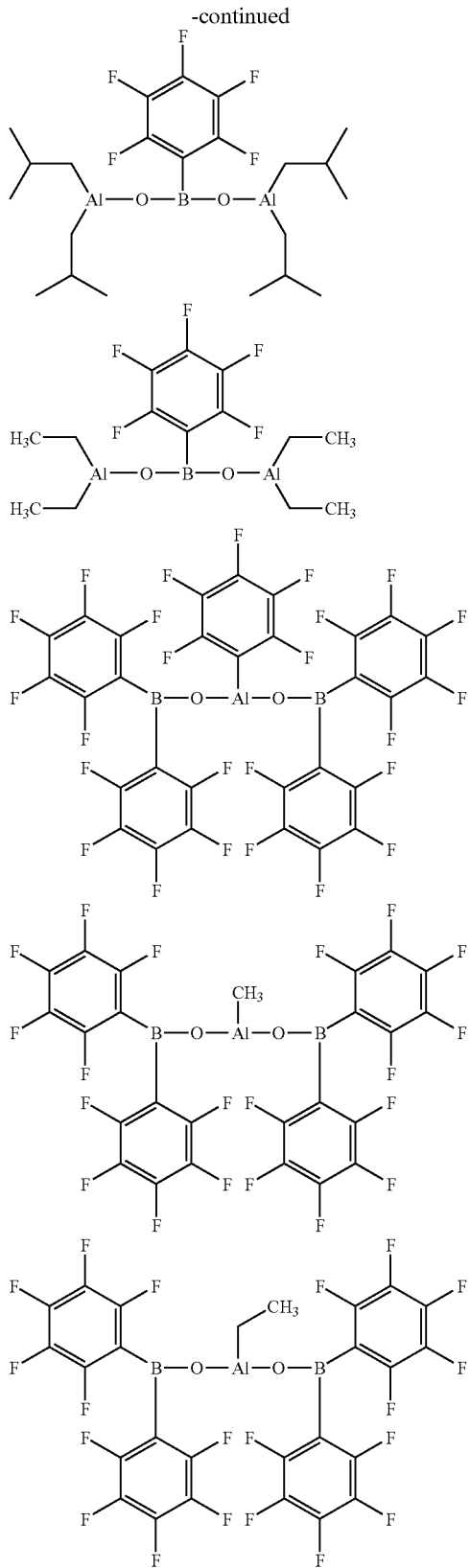

The organometallic compounds of the formula VII are preferably uncharged Lewis acids in which $M^{40}$ is lithium, magnesium and/or aluminium, in particular aluminium.

Examples of preferred organometallic compounds of the formula XII are trimethylaluminium, triethylaluminium, triisopropylaluminium, trihexylaluminium, trioctylaluminium, tri-n-butylaluminium, tri-n-propylaluminium, triisoprenylaluminium, dimethylaluminium monochloride, diethylaluminium monochloride, diisobutylaluminium monochloride, methylaluminium sesquichloride, ethylaluminium sesquichloride, dimethylaluminium hydride, diethylaluminium hydride, diisopropylaluminium hydride, dimethylaluminium trimethylsiloxide, dimethylaluminium triethylsiloxide, phenylalane, pentafluorophenylalane and o-tolylalane.

As further cocatalysts, which can be in unsupported or supported form, it is possible to use the compounds described in EP-A-924223, DE-A-19622207, EP-A-601830, EP-A-824112, EP-A-824113, EP-A-811627, WO 97/11775 and DE-A-19606167.

The support component of the catalyst system of the invention can be any organic or inorganic, inert solid, in particular a porous support such as talc, inorganic oxides and finely divided polymer powders (e.g. highly porous polyolefins such as polyethylene and polypropylene whose particle size and pore volume are similar to those of silica).

Suitable inorganic oxides may be found in main groups II-VI of the Periodic Table and transition groups III-IV of the Periodic Table of the Elements. Examples of oxides preferred as supports include silicon dioxide, aluminium oxide and also mixed oxides of the elements calcium, aluminium, silicon, magnesium, titanium and corresponding oxide mixtures, and also hydrotalcite. Other inorganic oxides which can be used either alone or in combination with the above-mentioned preferred oxidic supports are, for example, MgO, $ZrO_2$, $TiO_2$ or $B_2O_3$, to name only a few. The support materials used have a specific surface area in the range from 10 to 1000 m²/g, a pore volume in the range from 0.1 to 5 ml/g and a mean particle size of from 1 to 500 μm. Preference is given to supports having a specific surface area in the range from 50 to 500 μm, a pore volume in the range from 0.5 to 3.5 ml/g and a mean particle size in the range from 5 to 350 μm. Particular preference is given to supports having a specific surface area in the range from 200 to 400 m²/g, a pore volume in the range from 0.8 to 3.0 ml/g and a mean particle size of from 10 to 200 μm.

If the support material used naturally has a low moisture content or residual solvent content, dehydration or drying before use can be omitted. If this is not the case, as when silica gel is used as support material, dehydration or drying is advisable. Thermal dehydration or drying of the support material can be carried out under reduced pressure with simultaneous blanketing with inert gas (e.g. nitrogen). The drying temperature is in the range from 100 to 1000° C., preferably from 200 to 800° C. The parameter of pressure is not critical in this case. The duration of the drying process can be from 1 to 24 hours. Shorter or longer drying times are possible, provided that equilibrium with the hydroxyl groups on the support surface can be established under the chosen conditions, which normally takes from 4 to 8 hours. Dehydration or drying of the support material can also be carried out by chemical means, by reacting the adsorbed water and the hydroxyl groups on the surface with suitable passivating agents. Reaction with the passivating reagent enables the hydroxyl groups to be converted completely or partly into a form which does not lead to any adverse interaction with the catalytically active sites. Suitable passivating agents are, for example, silicon halides and silanes, e.g. silicon tetrachloride, chlorotrimethylsilane, dimethylaminotrichlorosilane, or organometallic compounds of aluminium, boron and magnesium, for example trimethylaluminium, triethylaluminium, triisobutylaluminium, triethylborane, dibutylmagnesium. The chemical dehydration or passivation of the support material is carried out, for example, by reacting a suspension of the support material in a suitable solvent with the passivating reagent in pure form or as a solution in a suitable solvent in the absence of air and moisture. Suitable solvents are, for example, aliphatic or aromatic hydrocarbons such as pentane, hexane, heptane, toluene or xylene. Passivation is carried out at temperatures in the range from 25° C. to 120° C., preferably from 50 to 70° C. Higher and lower temperatures are possible. The reaction time is from 30 minutes to 20 hours, preferably from 1 to 5 hours. After chemical dehydration has proceeded to completion, the support material is isolated by filtration under inert conditions, washed one or more times with suitable inert solvents as have been described above, and subsequently dried in a stream of inert gas or under reduced pressure.

Organic support materials such as finely divided polyolefin powders (e.g. polyethylene, polypropylene or polystyrene) can also be used and should likewise be freed of adhering moisture, solvent residues or other impurities by appropriate purification and drying operations before use.

To prepare the supported catalyst system, at least one of the above-described transition metal compounds of the formula Ia or Ib in a suitable solvent is brought into contact with at least one cocatalyst component, preferably giving a soluble reaction product, an adduct or a mixture 1.

The preparation obtained in this way is then mixed with the dehydrated or passivated support material, the solvent is removed and the resulting supported transition metal catalyst system is dried to ensure that all or most of the solvent is removed from the pores of the support material. The supported catalyst is obtained as a free-flowing powder.

A process for preparing a free-flowing and, if desired, prepolymerized transition metal catalyst system comprises the following steps:
a) preparation of a transition metal compound/cocatalyst mixture in a suitable solvent or suspension medium, with the transition metal component having one of the above-described structures,
b) application of the transition metal compound/cocatalyst mixture to a porous, preferably inorganic dehydrated support,
c) removal of the major part of the solvent from the resulting mixture,
d) isolation of the supported catalyst system,
e) if desired, prepolymerization of the resulting supported catalyst system with one or more olefinic monomer(s) to give a prepolymerized supported catalyst system.

Preferred solvents for the preparation of the transition metal compound/cocatalyst mixture are hydrocarbons and hydrocarbon mixtures which are liquid at the chosen reaction temperature and in which the individual components preferably dissolve. However, solubility of the individual components is not a prerequisite as long as it is ensured that the reaction product of transition metal compound and cocatalyst components is soluble in the solvent selected. Examples of suitable solvents include alkanes such as pentane, isopentane, hexane, heptane, octane and nonane; cycloalkanes such as cyclopentane and cyclohexane; and aromatics such as benzene, toluene, ethylbenzene and diethylbenzene. Very particular preference is given to toluene.

The amounts of aluminoxane and transition metal compound used in the preparation of the supported catalyst system can be varied over a wide range. Preference is given to a molar ratio of aluminium to transition metal in the transition metal compounds of from 10:1 to 1000:1, very particularly preferably from 50:1 to 500:1. In the case of methylaluminoxane, preference is given to using 30% strength solutions in toluene, but the use of 10% strength solutions is also possible. Preactivation is carried out by suspending the transition metal compound in the form of a solid in a solution of the aluminoxane in a suitable solvent. It is also possible to dissolve the transition metal compound separately in a suitable solvent and subsequently to combine this solution with the aluminoxane solution. Preference is given to using toluene.

The preactivation time is from 1 minute to 200 hours.

The preactivation can take place at room temperature (25° C.). The use of higher temperatures can in individual cases shorten the preactivation time required and effect an additional increase in activity. In this case, "higher temperatures" means a range from 50 to 100° C.

The preactivated solution or the transition metal compound/catalyst mixture is subsequently combined with an inert support material, usually silica gel, which is present in the form of a dry powder or as a suspension in one of the abovementioned solvents. The support material is preferably used as a powder. The order of addition is immaterial. The preactivated transition metal compound/cocatalyst solution or the transition metal compound/cocatalyst mixture can be added to the initially charged support material, or else the support material can be introduced into the initially charged solution.

The volume of the preactivated solution or of the transition metal compound/cocatalyst mixture can exceed 100% of the total pore volume of the support material used or else can be up to 100% of the total pore volume. The temperature at which the preactivated solution or the transition metal compound/cocatalyst mixture is brought into contact with the support material can vary in the range from 0 to 100° C. Lower or higher temperatures are also possible. All or most of the solvent is subsequently removed from the supported catalyst system, with the mixture being able to be stirred and, if appropriate, also heated. Preference is given to removing both the visible proportion of the solvent and also the proportion present in the pores of the support material. Removal of the solvent can be carried out in a conventional way under reduced pressure and/or with flushing with inert gas. In the drying procedure, the mixture can be heated until the free solvent has been removed, which usually takes from 1 to 3 hours at a preferred temperature in the range from 30 to 60° C. The free solvent is the visible proportion of solvent in the mixture. For the purposes of the present invention, residual solvent is the proportion which is enclosed in the pores. As an alternative to complete removal of the solvent, the supported catalyst system can also be dried only to a particular residual solvent content, with the free solvent having been completely removed. The supported catalyst system can subsequently be washed with a low-boiling hydrocarbon such as pentane or hexane and dried again.

The supported catalyst system prepared according to the invention can either be used directly for the polymerization of olefins or can be prepolymerized with one or more olefinic monomers before being used in a polymerization process. The procedure for prepolymerization of supported catalyst systems is described, for example, in WO 94/28034.

A small amount of an olefin, preferably an a-olefin (for example vinylcyclohexane, styrene or phenyidimethylvinylsilane), as modifying component or an antistatic (as described in U.S. Ser. No. 08/365280) can be added as additive during or after the preparation of the supported catalyst system. The molar ratio of additive to nonmetallocene compound I is preferably from 1:1000 to 1000:1, very particularly preferably from 1:20 to 20:1.

The present invention also provides a process for preparing a polyolefin by polymerization of one or more olefins in the presence of the catalyst system of the invention comprising at least one transition metal component of the formula VII. For the purposes of the present invention, the term polymerization encompasses both homopolymerization and copolymerization.

Preference is given to polymerizing olefins of the formula $R_m$—CH=CH—$R_n$, where $R_m$ and $R_n$ are identical or different and are each a hydrogen atom or a carbon-containing radical having from 1 to 20 carbon atoms, in particular from 1 to 10 carbon atoms, and $R_m$ and $R_n$ together with the atoms connecting them can form one or more rings.

Examples of such olefins are 1-olefins having 2–20, preferably from 2 to 10, carbon atoms, e.g. ethene, propene, 1-butene, 1-pentene, 1-hexene, 4-methyl-1-pentene or 1-octene, styrene, dienes such as 1,3-butadiene, 1,4-hexadiene, vinylnorbornene, norbornadiene, ethylnorbornadiene and cyclic olefins such as norbornene, tetracyclododecene or methylnorbornene. In the process of the invention, preference is given to homopolymerizing ethene or propene, or copolymerizing propene with ethene and/or with one or more 1-olefins having from 4 to 20 carbon atoms, e.g. butene, hexene, styrene or vinylcyclohexane, and/or one or more dienes having from 4 to 20 carbon atoms, e.g. 1,4-butadiene, norbornadiene, ethylidenenorbornene or ethylnorbornadiene. Examples of such copolymers are ethene/propene copolymers, ethene/norbornene copolymers, ethene/styrene copolymers and ethene/propene/1,4-hexadiene terpolymers.

The polymerization is carried out at a temperature of from 0 to 300° C., preferably from 50 to 200° C., very particularly preferably 50–80° C. The pressure is from 0.5 to 2000 bar, preferably from 5 to 64 bar.

The polymerization can be carried out in solution, in bulk, in suspension or in the gas phase, continuously or batchwise, in one or more stages.

The catalyst system prepared according to the invention can be used as sole catalyst component for the polymerization of olefins having from 2 to 20 carbon atoms, or can be preferably used in combination with at least one alkyl compound of the elements of main groups I to III of the Periodic Table, e.g. an aluminium alkyl, magnesium alkyl or lithium alkyl or an aluminoxane. The alkyl compound is added to the monomer or suspension medium and serves to free the monomer of substances which could adversely affect the catalyst activity. The amount of alkyl compound added depends on the quality of the monomers used.

Hydrogen is added, if necessary, as molar mass regulator and/or to increase the activity.

The catalyst system can be introduced into the polymerization system in pure form or can be admixed with inert components such as paraffins, oils or waxes to improve meterability. In addition, an antistatic can be introduced into the polymerization system either together with or separately from the catalyst system used. The polymers prepared using the catalyst system of the invention display a uniform particle morphology and contain no fines. In the polymerization using the catalyst system of the invention, no deposits or caked material are formed.

The invention claimed is:

1. A compound of the formulae Ia and Ib,

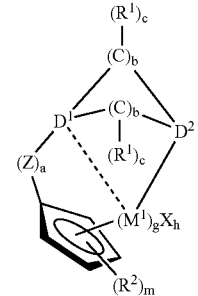

Formula Ia

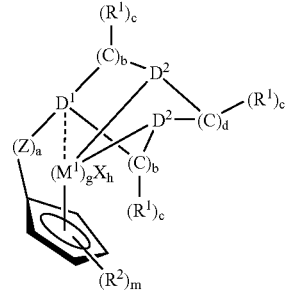

Formula Ib where $M^1$ is a metal of groups III to X of the Periodic Table of the Elements, the radicals $D^1$ are identical or different and are each a donor atom of group XV of the Periodic Table of the Elements, and the radicals $D^2$ are identical or different and are each a donor atom of group XV of the Periodic Table of the Elements, and Z is a bridging structural element between the donor atom $D^1$ and the pentacoordinating cyclic system and the radicals X are identical or different and are each a hydrogen atom, a C1–$C_{20}$-hydrocarbon group or a halogen atom or $OR^3$, $SR^3$, $OSO_2R^3$, $OSi(R^3)_3$, $Si(R^3)_3$, $P(R^3)_2$, $P(R^3)_3$, $NCR^3$, $N(R^3)_3$, $B(R^3)_4$, substituted or unsubstituted pyridine or $N(R^3)_2$, and the radicals $R^1$ are identical or different and are each a hydrogen atom, a $C_1$–$C_{20}$-alkyl group, a $C_6$–$C_{20}$-aryl group, a $C_7$–$C_{20}$-alkylaryl group, a C7-$C_{10}$-arylalkyl group, a $C_2$–$C_{20}$-alkenyl group, a $C_2$–$C_{20}$-alkynyl group or a halogen-containing $C_1$–$C_{20}$-alkyl group, $C_6$–$C_{20}$-aryl group, $C_7$–$C_{30}$-alkylaryl group, $C_7$–$C_{30}$-arylalkyl group, $C_2$–$C_{20}$-alkenyl group, $C_2$–$C_{20}$-alkynyl group or a heteroatom-containing $C_1$–$C_{20}$-alkyl group, $C_6$–$C_{20}$-aryl group, $C_7$–$C_{20}$-alkylaryl group, $C_7$–$C_{30}$-arylalkyl group, $C_2$–$C_{20}$-alkenyl group, $C_2$–$C_{20}$-alkynyl group or $Si(R^3)_3$, where one or more radicals $R^1$ together with one or more radicals $R^1$ may form a monocyclic or polycyclic ring system, and the radicals $R^2$ are identical or different and are each a hydrogen atom, $Si(R^3)_3$, a $C_1$–$C_{30}$ group which together with the cyclopentadienyl ring may form an azapentalene, diiapentalene or thiapentalene or phosphapentalene, or two or more radicals $R^2$ may be joined to one another so that the radicals $R^2$ and the atoms of the cyclopentadienyl ring which connect than form a $C_4$–$C_{24}$ ring system which may in turn be substituted by $R^3$, the radicals $R^3$ are identical or different and are each a hydrogen atom, a halogen atom, a $C_1$–$C_{10}$-alkyl group, a $C_6$–$C_{20}$-aryl group, a $C_7$–$C_{20}$-alkylaryl group, a $C_7$–$C_{30}$-arylalkyl group, a $C_2$–$C_{20}$-alkenyl group, a $C_2$–$C_{20}$-alkynyl group or a halogen-containing $C_1$–$C_{20}$-alkyl group, $C_6$–$C_{20}$-aryl group, $C_7$–$C_{20}$-alkylaryl group, $C_7$–$C_{30}$-arylalkyl group, $C_2$–$C_{20}$-alkenyl group, $C_2$–$C_{20}$-alkynyl group or a heteroatom-containing $C_1$–$C_{20}$-alkyl group, $C_6$–$C_{20}$-aryl group, $C_7$–$C_{20}$-alkylaryl group, $C_7$–$C_{30}$-arylalkyl group, $C_2$–$C_{20}$-alkenyl group, $C_2$–$C_{20}$-alkynyl group, and a is an integer from 0 to 10, and when a=0, $D^1$ forms a covalent bond to the pentacoordinating cyclic system, and the indices b are identical or different and are each an integer from 1 to 10, and the indices c are identical or different and are each an integer from 1 to 10, and d is an integer from 1 to 10, and g is an integer from 1 to 3, and h is an integer from 1 to 4, and m is 4.

2. The compound according to claim 1, characterized in that Z is a group $CH_2$, $C(CH_3)H$, $C(CH_3)_2$, $C(C_2H_5)H$, $C(C_2H_5)(CH_3)$, $C(C_2H_5)_2$, $C(phenyl)H$, $C(phenyl)(CH_3)$, $C(phenyl)(C_2H_5)$, $C(phenyl)_2$, $CH_2CH_2$, $C(CH_3)HCH_2$, $C(CH_3)_2CH_2$, $C(CH_3)_2C(CH_3)H$, $C(CH_3)_2C(CH_3)_2$, $C(phenyl)HC(phenyl)H$, $C(CH_2)_2$, $C(CH_2)_3$, $C(CH_2)_4$, $C(CH_2)_5$, $C(CH_2)_6$, o-$C_6H_4$, m-$C_6H_4$, p-$C_6H_4$, o-$C_{10}H_6$, m-$C_{10}H_6$, p-$C_{10}H_6$, 2,2'-(1,1'-bipheny), 2,2'-binaphthyl), $Si(CH_3)_2$, $Si(CH_3)(Si(CH_3)_3$, $Si(Si(CH_3)_3)_2$, $Si(phenly)Me$, $Si(phenly)_2$, $Si(CH_3)_2Si(CH_3)_2$, $Si(CH_2)_2$, $Si(CH_2)_3$, $Si(CH_2)_4$, $Si(CH_2)_5$, $Si(CH_2)_6$ and $Ge(CH_3)_2$.

3. The compound according to claim 1, characterized in that $M^1$ is metal selected from the group consisting of Sc, Y, La, Ti, Zr, Hf, V, Nb, Ta, Cr, Mo, W, Mn, Re, Fe, Ru, Co, Rh, Ir, Ni, Pd and Pt and the radicals $D^1$ are identical or different and are each a donor atom of group XV of the Periodic Table of the Elements, and the radicals $D^2$ are identical or different and are each a donor atom of the group XV of the Periodic Table of the Elements, and Z is a bridging structural element between the donor atom $D^1$ and the pentacoordinating cyclic system and the radicals X are identical or different and are each a hydrogen atom, a $C_1$–$C_{10}$-hydrocarbon group, $C_6$–$C_{10}$-aryl, $C_7$–$C_{10}$-alkylaryl, $C_7$–$C_{10}$-arylalkyl $C_2$–$C_{10}$-alkenyl, $C_2$–$C_{10}$-alkynyl or a halogen atom or $OR^3$, $SR^3$, $OSO_2R^3$, $OSi(R^3)_3$, $Si(R^3)_3$, $P(R^3)_2$, $P(R^3)_3$, $NCR^3$, $N(R^3)_3$, $B(R^3)_4$, substituted or unsubstituted pyridine or $N(R^3)_2$, and the radicals $R^1$ are identical or different and are each a hydrogen atom, a $C_1$–$C_{10}$-alkyl group, a $C_6$–$C_{10}$-aryl group, a $C_7$–$C_{10}$-alkylaryl group, a $C_7$–$C_{10}$-arylalkyl group, a $C_2$–$C_{10}$-alkenyl group, a $C_2$–$C_{10}$-alkynyl group or a halogen-containing $C_1$–$C_{10}$-alkyl group, $C_6$–$C_{10}$-aryl group, $C_7$–$C_{10}$-alkylaryl group, $C_7$–$C_{10}$-arylalkyl group, $C_2$–$C_{10}$-alkenyl group, $C_2$–$C_{10}$-alkynyl group or a heteroatom-containing $C_1$–$C_{10}$-alkyl group, $C_6$–$C_{10}$-aryl group, $C_7$–$C_{10}$-alkylaryl group, $C_7$–$C_{10}$-arylalkyl group, $C_2$–$C_{10}$-alkenyl group, $C_2$–$C_{10}$-alkynyl group or $Si(R^3)_3$, where one or more radicals $R^1$ together with one or more radicals $R^1$ may form a monocyclic or polycyclic ring system, and the radicals $R^2$ are identical or different and are each a hydrogen atom, $Si(R^3)_3$, a $C_1$–$C_{30}$ group, $C_2$–$C_{25}$-alkenyl, $C_3$–$C_{15}$-alkylalkenyl, $C_6$–$C_{24}$-aryl, $C_5$–$C_{24}$-heteroaryl which together with the cyclopentadienyl ring form an azapentalene, thiapentalene or phosphapentalene, $C_7$–$C_{30}$-arylalkyl, $C_7$–$C_{30}$-alkylaryl, fluorinated $C_1$–$C_{25}$-alkyl, fluorinated $C_6$–$C_{24}$-aryl, fluorinated $C_7$–$C_{30}$-arylalkyl, fluorinated $C_7$–$C_{30}$-alkylaryl or $C_1$–$C_{12}$-alkoxy, or two or more radicals $R^2$ may be joined to one another so that the radicals $R^2$ and the atoms of the cyclopentadienyl ring which connect them may form a $C_4$–$C_{24}$ ring system which may in turn be substituted by $R^3$, the radicals $R^3$ are identical or different and are each a hydrogen atom, a halogen atom, a $C_1$–$C_{10}$-alkyl group, a $C_6$–$C_{10}$-aryl group, a $C_7$–$C_{10}$-alkylaryl group, a $C_7$–$C_{10}$-arylalkyl group, a $C_2$–$C_{10}$-alkenyl group, a $C_2$–$C_{10}$-alkynyl group or a halogen-containing $C_1$–$C_{10}$-alkyl group, $C_6$–$C_{10}$-aryl group, $C_7$–$C_{10}$-alkylaryl group, $C_7$–$C_{20}$-arylalkyl group, $C_2$–$C_{10}$-alkenyl group, $C_2$–$C_{10}$-alkynyl group or a heteroatom-containing $C_1$–$C_{10}$-alkyl group, $C_6$–$C_{10}$-aryl group, $C_7$–$C_{10}$-alkylaryl group, $C_7$–$C_{20}$-arylalkyl group, $C_2$–$C_{10}$-alkenyl group, $C_2$–$C_{10}$-alkynyl group, and a is an integer from 0 to 5, and when a=0, $D^1$ forms a covalent bond to the pentacoordinating cyclic system, and the indices b are identical or different and are each an integer from 1 to 7, and the indices c are identical or different and are each an integer from 1 to 10, and d is an integer from 1 to 7, and g is an integer from 1 to 2, and h is an integer from 1 to 4, and m is 4.

4. The compound according to claim 1, characterized in that $M^1$ is Ti, Zr, Hf, V, Nb, Cr, Mo, Mn, Fe, Ru, Co, Rh or Ni, and the radicals $D^1$ are identical or different and are each N or P and the radicals $D^2$ are identical or different and are each N or P and Z is a bridging structural element the donor atom $D^1$ and the pentacoordinating cyclic system and the radicals X are identical or different and are each a hydrogen atom, fluoride, chloride, bromide, iodide, methyl, ethyl, butyl, benzyl, tolyl, ethenyl, ethynyl, phenoxide, dimethylamide, diphenylphosphine, triphenylphosphine, tetrakis(pentafluorophenyl)borate or pyridyl, and the radicals $R^1$ are identical or different and are each a hydrogen atom, a silyll group, a $C_1$–$C_{10}$-alkyl group, a $C_6$–$C_{10}$-aryl group, a $C_5$–$C_{10}$ heteroaryl group, a $C_5$–$C_{10}$, heterocyclic group, a $C_7$–$C_{10}$ alkylaryl group, a $C_2$–$C_{10}$ alkynyl group, a halogenated $C_2$–$C_{10}$ alkyl group, where one or more radicals $R^1$ together with one or more radicals $R^1$ may form a monocyclic or polycyclic ring system which may be substituted by one or more radicals $R^3$, in particular piperazine, 1,4-dihydropyrazine, 2,6-dimethyl-1,4-dihydropyrazine, 2,6-diphenyl-1,4-dihydropyrazine, 5,10-dihydrophenazine, 2,3-dihydrobenzimidazole, 2,2-dimetbyl-2,3-dihydrobenzimidazole, 2,2-di-i-propyl-2,3-dihydrobenzimidazole, or 1,3,5-triazinane, and the radicals $R^2$ are identical or different and are each a hydrogen atom, a silyll group, a $C_1$–$C_{10}$alkyl group, a $C_6$–$C_{10}$aryl group, a heteroaryl group, a $C_5$–$C_{10}$ heterocyclic group, a $C_7$–$C_{10}$ alkylaryl group, a $C_2$–$C_{10}$ alkenyl group, a $C_2$–$C_{10}$ alkynyl group, a halogenated $C_1$–$C_{10}$ alkyl group, $C_5$–$C_{10}$ heteroaryl group which together with the cyclopentadienyl ring may form an azapentalene, thiapentalene or pbosphapentalene, or two or more radicals $R^2$ may be joined to one another so that the radicals $R^2$ and the atoms of the cyclopentadienyl ring which connect them form a polycyclic ring system, e.g. indenyl, fluorenyl or cyclopentaphenanthrene which may in turn be substituted by $R^3$, and the radicals $R^3$ are identical or different and are each a hydrogen atom, a silyll group such as trimethylsilyll, triethylsilyll, tri-i-propylsilyll ortriphenylsilyll, a $C_1$–$C_{10}$ alkyl group, a $C_6$–$C_{10}$ aryl group, a $C_5$–$C_{10}$ heteroaryl group, a $C_5$–$C_{10}$-heterocyclic group, a $C_7$–$C_{10}$-alkylaryl group, a $C_2$–$C_{10}$-alkenyl group, a $C_2$–$C_{10}$-alkynyl group, a halogenated $C_1$–$C_{10}$-alkyl group, a $C_5$–$C_{10}$-heteroaryl group, and a is an integer from 0 to 2, and when a=0, $D^1$ forms a covalent bond to the pentacoordinating cyclic system, and the indices b are identical or different and are each an integer from 1 to 7, and the indices c are identical or different and are each an integer from 1 to 10, and d is an integer from 1 to 4, and g is 1 and, h is an integer from 1 to 3, and m is 4.

5. Catalyst system comprising at least one compound according to claim 1 and at least one cocatalyst.

6. Catalyst system comprising at least one compound according to claim 1 and at least one support.

7. Catalyst system according to claim 5, characterized in that the cocatalyst is at least one compound of the aluminoxane type or at least one Lewis acid or at least one ionic compound which converts the compound according to claim 1 into a cationic compound.

8. A process for preparing polyolefins comprising the steps of:

providing one or more olefins;

providing a catalyst system according claim 5; and polymerizing one or more olefins in the presence of said catalyst system.

9. The process for preparing polyolefins according to claim 8, characterized in that the polymerization is a homopolymerization or a copolymerization of one or more olefins.

10. Catalyst system comprising at least one compound according to claim 2 and at least one cocatalyst.

11. Catalyst system according to claim 10, characterized in that the cocatalyst is at least one compound of the aluminoxane type or at least one Lewis acid or at least one ionic compound which converts the compound according to claim 1 into a cationic compound.

12. A process for preparing polyolefins comprising the steps of:

providing one or more olefins;

providing a catalyst system according claim 10; and polymerizing one or more olefins in the presence of said catalyst system.

13. Catalyst system comprising at least one compound according to claim 3 and at least one cocatalyst.

14. Catalyst system according to claim 13, characterized in that to cocatalyst is at least one compound of the aluminoxane type or at least one Lewis acid or at least one ionic compound which converts the compound according to claim 1 into a cationic compound.

15. A process for preparing polyolefins comprising the steps of:

providing one or more olefins;

providing a catalyst system according claim 13; and polymerizing one or more olefins in the presence of said catalyst system.

16. Catalyst system comprising at least one compound according to claim 4 and at least one cocatalyst.

17. Catalyst system according to claim 16, characterized in that the cocatalyst is at least one compound of the aluminoxane type or at least one Lewis acid or at least one ionic compound which converts the compound according to claim 1 into a cationic compound.

18. A process for preparing polyolefins comprising the steps of:

providing one or more olefins;

providing a catalyst system according claim 16; and polymerizing one or more olefins in the presence of said catalyst system.

19. The compound according to claim 3, where the $C_1$–$C_{10}$-hydrocarbon group is a $C_1$–$C_{10}$-alkyl; and the radicals $R^2$ of the $C_1$–$C_{30}$ group is selected from the group of $C_1$–$C_{25}$-alkyl, methyl, ethyl, tert-butyl, cyclohexyl or octyl.

20. The compound according to claim 4, where to radical $R^1$ silyll group is selected from the group of: trimethylsilyl, triethylsilyl, tri-i-propylsilyl or triphenylsilyl;

the $C_1$–$C_{10}$ alkyl group is selected from the group of: methyl, ethyl, propyl, butyl, i-propyl, s-butyl or t-butyl;

the $C_6$–$C_{10}$ aryl group is selected from the group of: phenyl, tolyl, xylenyl, mesityl, p-methoxyphenyl, p-t-butylphenyl or naphthyl;

the $C_5$–$C_{10}$ heteroaryl group is selected from to group of: pyridyl, pyridazinyl, pyrimidinyl, pyrazinyl, quinolinyl or borataphenyl;

the $C_5$–$C_{10}$ heterocyclic group is selected from the group of: furyl, benzofuyl or thiophenyl;

the $C_7$–$C_{10}$ alkylaryl group is selected from to group of: a $C_2$–$C_{10}$ alkenyl group or ethenyl;

the $C_2$–$C_{10}$ alkynyl is selected from the group of: ethynyl or propynyl;

the halogenated $C_2$–$C_{10}$ alkyl group is selected from the group of: trifluoromethyl or pentafluoroethyl;

where the radicals $R^2$ is a silyll group selected from the group of: trimethylsilyll, triethylsilyll, tri-i-propylsilyll or triphenylsilyll, the $C_1$–$C_{10}$ alkyl group is selected from the group of: methyl, ethyl, propyl, butyl, i-propyl, s-butyl or t-butyl, the $C_6$–$C_{10}$ aryl group is selected from the group of: phenyl, tolyl, xylenyl, mesityl, p-methoxyphenyl, p-t-butylphenyl or naphthyl, the heteroaryl group is selected from the group of: pyridyl, pyridazinyl, pyrimidinyl, pyrazinyl, quinolinyl or borataphenyl, the $C_5$–$C_{10}$ heterocyclic group is selected from the group of: furyl, benzofuryl or thiophenyl, the $C_7$–$C_{10}$ alkylaryl group is benzyl, the $C_2$–$C_{10}$ alkenyl group is ethenyl, the $C_2$–$C_{10}$ alkynyl group is ethynyl, the halogenated $C_1$–$C_{10}$ alkyl group selected from the group of: trifluoromethyl or pentafluoroethyl;

where the radicals R³ are a silyll group such as trimethylsilyll, triethylsilyll, tri-i-propylsilyll or triphenylsilyll, $C_1$–$C_{10}$ alkyl group, is select from the group of: methyl, ethyl, propyl, butyl, i-propyl, s-butyl or t-butyl;

the $C_6$–$C_{10}$-aryl group is select from the group of: phenyl, tolyl, xylenyl, mesityl, p-methoxyphenyl, p-t-butylphenyl or naphthyl;

the $C_5$–$C_{10}$-heteroaryl group is select from the group of: pyridyl, pyridazinyl, pyrimidinyl, pyrazinyl, quinolinyl or borataphenyl;

the $C_5$–$C_{10}$-heterocyclic group is select from the group of: furyl, benzofuryl or thiophenyl, the $C_7$–$C_{10}$-alkylaryl group is benzyl;

the $C_2$–$C_{10}$-alkenyl group is ethenyl;

the $C_2$–$C_{10}$-alkynyl group is ethynyl, the halogenated $C_1$–$C_{10}$-alkyl group is select from the group of: trifluoromethyl or pentafluoroethyl.

\* \* \* \* \*